(12) United States Patent
Alessi et al.

(10) Patent No.: US 8,926,595 B2
(45) Date of Patent: Jan. 6, 2015

(54) DEVICES, FORMULATIONS, AND METHODS FOR DELIVERY OF MULTIPLE BENEFICIAL AGENTS

(71) Applicants: Thomas R. Alessi, Hayward, CA (US); Karling Alice Leung, Oakland, CA (US); Ryan D. Mercer, Dublin, CA (US); Cristina G. Negulescu, Santa Clara, CA (US); Catherine M. Rohloff, Los Altos, CA (US); Bing Yang, Redwood City, CA (US)

(72) Inventors: Thomas R. Alessi, Hayward, CA (US); Karling Alice Leung, Oakland, CA (US); Ryan D. Mercer, Dublin, CA (US); Cristina G. Negulescu, Santa Clara, CA (US); Catherine M. Rohloff, Los Altos, CA (US); Bing Yang, Redwood City, CA (US)

(73) Assignee: Intarcia Therapeutics, Inc., Boston, MA (US)

( * ) Notice: Subject to any disclaimer, the term of this patent is extended or adjusted under 35 U.S.C. 154(b) by 212 days.

(21) Appl. No.: 13/689,410

(22) Filed: Nov. 29, 2012

(65) Prior Publication Data

US 2013/0090287 A1 Apr. 11, 2013

Related U.S. Application Data

(62) Division of application No. 12/378,341, filed on Feb. 12, 2009, now Pat. No. 8,343,140.

(60) Provisional application No. 61/065,692, filed on Feb. 13, 2008.

(51) Int. Cl.
| | | |
|---|---|---|
| A61K 9/22 | (2006.01) | |
| A61K 47/32 | (2006.01) | |
| A61K 9/00 | (2006.01) | |
| A61K 9/50 | (2006.01) | |
| A61K 38/22 | (2006.01) | |
| A61K 38/26 | (2006.01) | |
| A61K 45/06 | (2006.01) | |
| A61K 9/16 | (2006.01) | |

(52) U.S. Cl.
CPC .............. *A61K 47/32* (2013.01); *A61K 9/0004* (2013.01); *A61K 9/0024* (2013.01); *A61K 9/5084* (2013.01); *A61K 38/22* (2013.01); *A61K 38/26* (2013.01); *A61K 45/06* (2013.01); *A61K 38/2278* (2013.01); *A61K 9/1617* (2013.01); *A61K 9/1623* (2013.01)
USPC ...................................................... 604/892.1

(58) Field of Classification Search
USPC ........................................................ 604/19
See application file for complete search history.

(56) References Cited

U.S. PATENT DOCUMENTS 5,118,666 A 6/1992 Habener
5,120,712 A 6/1992 Habener (Continued)

OTHER PUBLICATIONS

"Abstracts 2007"; Diabetologia; Clinical and Experimental Diabetes and Metabolism; Springer; Berlin, Germany; vol. 50, No. 1; Aug. 21, 2007; p. S243; paragraph [0586].

(Continued)

*Primary Examiner* — Jason Flick
(74) *Attorney, Agent, or Firm* — Cooley LLP; Ivor Elrifi

(57) ABSTRACT

The present invention relates to osmotic delivery devices, formulations, and methods for delivery of two or more beneficial agents. In one aspect, the present invention provides osmotic delivery devices useful for substantially concurrent administration of two or more beneficial agents. In another aspect, the present invention provides beneficial agent formulations for use in the osmotic delivery devices. The formulations include formulations wherein beneficial agents are soluble in the vehicle, suspension formulations comprising particle formulations of one or more beneficial agent, and combinations thereof. Further, methods for treatment of a variety of diseases or conditions using two or more beneficial agents are disclosed, wherein the methods are preferably practiced using the osmotic delivery devices and/or formulations of the invention.

31 Claims, 9 Drawing Sheets

(56) References Cited

U.S. PATENT DOCUMENTS

| | | | |
|---|---|---|---|
| 5,545,618 A | 8/1996 | Buckley et al. |
| 5,609,885 A | 3/1997 | Rivera et al. |
| 5,614,492 A | 3/1997 | Habener |
| 5,728,396 A | 3/1998 | Peery et al. |
| 5,904,935 A | 5/1999 | Eckenhoff et al. |
| 5,932,547 A | 8/1999 | Stevenson et al. |
| 5,958,909 A | 9/1999 | Habener |
| 5,972,370 A | 10/1999 | Eckenhoff et al. |
| 5,985,305 A | 11/1999 | Peery et al. |
| 5,997,527 A | 12/1999 | Gumucio et al. |
| 6,113,938 A | 9/2000 | Chen et al. |
| 6,124,261 A | 9/2000 | Stevenson et al. |
| 6,130,200 A | 10/2000 | Brodbeck et al. |
| 6,132,420 A | 10/2000 | Dionne et al. |
| 6,156,331 A | 12/2000 | Peery et al. |
| 6,190,350 B1 | 2/2001 | Davis et al. |
| 6,217,906 B1 | 4/2001 | Gumucio et al. |
| 6,235,712 B1 | 5/2001 | Stevenson et al. |
| 6,261,584 B1 | 7/2001 | Peery et al. |
| 6,270,787 B1 | 8/2001 | Ayer |
| 6,287,295 B1 | 9/2001 | Chen et al. |
| 6,331,311 B1 | 12/2001 | Brodbeck et al. |
| 6,375,978 B1 | 4/2002 | Kleiner et al. |
| 6,395,292 B2 | 5/2002 | Peery et al. |
| 6,468,961 B1 | 10/2002 | Brodbeck et al. |
| 6,471,688 B1 * | 10/2002 | Harper et al. ............ 604/892.1 |
| 6,508,808 B1 | 1/2003 | Carr et al. |
| 6,524,305 B1 | 2/2003 | Peterson et al. |
| 6,544,252 B1 | 4/2003 | Theeuwes et al. |
| 6,579,851 B2 | 6/2003 | Goeke et al. |
| 6,635,268 B2 | 10/2003 | Peery et al. |
| 6,673,767 B1 | 1/2004 | Brodbeck et al. |
| 6,682,522 B2 | 1/2004 | Carr et al. |
| 6,703,359 B1 | 3/2004 | Young et al. |
| 6,730,328 B2 | 5/2004 | Maskiewicz et al. |
| 6,840,931 B2 | 1/2005 | Peterson et al. |
| 6,849,708 B1 | 2/2005 | Habener |
| 6,923,800 B2 | 8/2005 | Chen et al. |
| 6,939,556 B2 | 9/2005 | Lautenbach |
| 6,956,026 B2 | 10/2005 | Beeley et al. |
| 6,976,981 B2 | 12/2005 | Ayer |
| 6,997,922 B2 | 2/2006 | Theeuwes et al. |
| 7,014,636 B2 | 3/2006 | Gilbert |
| 7,074,423 B2 | 7/2006 | Fereira et al. |
| 7,112,335 B2 | 9/2006 | Lautenbach |
| 7,163,688 B2 | 1/2007 | Peery et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,407,499 B2 | 8/2008 | Trautman |
| 7,459,432 B2 | 12/2008 | Cowley et al. |
| 7,666,835 B2 | 2/2010 | Bloom et al. |
| 7,741,269 B2 | 6/2010 | Young et al. |
| 7,825,091 B2 | 11/2010 | Bloom et al. |
| 7,879,794 B2 | 2/2011 | Weyer et al. |
| 7,928,065 B2 | 4/2011 | Young et al. |
| 8,058,233 B2 | 11/2011 | Cowley et al. |
| 8,101,576 B2 | 1/2012 | Bloom |
| 8,202,836 B2 | 6/2012 | Moore et al. |
| 8,217,001 B2 | 7/2012 | Cowley et al. |
| 8,263,545 B2 | 9/2012 | Levy et al. |
| 8,263,736 B2 | 9/2012 | Bloom |
| 8,273,713 B2 | 9/2012 | Pittner et al. |
| 8,278,267 B2 | 10/2012 | Weyer et al. |
| 8,288,338 B2 | 10/2012 | Young et al. |
| 8,298,561 B2 | 10/2012 | Alessi et al. |
| 8,299,025 B2 | 10/2012 | Alessi et al. |
| 2002/0141985 A1 | 10/2002 | Pittner et al. |
| 2004/0224903 A1 | 11/2004 | Berry et al. |
| 2005/0008661 A1 | 1/2005 | Fereira et al. |
| 2005/0010196 A1 | 1/2005 | Fereira et al. |
| 2005/0101943 A1 | 5/2005 | Ayer et al. |
| 2005/0112188 A1 | 5/2005 | Eliaz et al. |
| 2005/0175701 A1 | 8/2005 | Pan et al. |
| 2005/0215475 A1 | 9/2005 | Ong et al. |
| 2005/0266087 A1 | 12/2005 | Junnarkar et al. |
| 2005/0276856 A1 | 12/2005 | Fereira et al. |
| 2006/0014678 A1 | 1/2006 | Cowley et al. |
| 2006/0094652 A1 | 5/2006 | Levy et al. |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0293232 A1 * | 12/2006 | Levy et al. ............ 514/12 |
| 2007/0027105 A1 | 2/2007 | Junnarkar et al. |
| 2007/0281024 A1 | 12/2007 | Lautenbach et al. |
| 2008/0020016 A1 | 1/2008 | Li et al. |
| 2008/0064636 A1 | 3/2008 | Bloom et al. |
| 2008/0091176 A1 | 4/2008 | Alessi et al. |
| 2008/0207512 A1 | 8/2008 | Roth et al. |
| 2008/0312157 A1 | 12/2008 | Levy et al. |
| 2009/0036364 A1 | 2/2009 | Levy et al. |
| 2009/0074734 A1 | 3/2009 | Rottiers |
| 2009/0156474 A1 | 6/2009 | Roth et al. |
| 2009/0186817 A1 | 7/2009 | Ghosh et al. |
| 2009/0202481 A1 | 8/2009 | Li et al. |
| 2009/0209460 A1 | 8/2009 | Young et al. |
| 2009/0210019 A1 | 8/2009 | Kim et al. |
| 2009/0286723 A1 | 11/2009 | Levy et al. |
| 2010/0092566 A1 | 4/2010 | Alessi et al. |
| 2011/0076317 A1 | 3/2011 | Alessi et al. |
| 2011/0152181 A1 | 6/2011 | Alsina-Fernandez et al. |
| 2011/0152182 A1 | 6/2011 | Alsina-Fernandez et al. |

OTHER PUBLICATIONS

"Gut Signals and Energy Balance: Ghrelin, Peptide YY, Leptin, and Amylin (Slides With Transcript)," by George A. Bray, MD, presented through Medscape CME, "The Diabetes-Obesity Continuum: The Growing Body of Evidence for a Multi-hormonal Approach to Treatment; Carol Hatch Wysham, MD, FACP, FACE, Chair; Stephen L. Aronoff, MD, FACE; George A. Bray, MD, MACE"; Release Date: Dec. 19, 2007.

PCT International Search Report for PCT/US2009/000916, dated Aug. 12, 2009 (4 pages).

PCT Written Opinion of the International Searching Authority (PCT Rule 43bis.1) for PCT/US2009/000916.

Roth, J.D., et al., "Combination therapy with amylin and peptide YY[3-36] in obese rodents: anorexigenic synergy and weight loss additivity," Endocrinology, Dec. 2007;148(12):6054-61.

Smith,Steven R., M.D., Professor Pennington Biomedical Research Center, LSU System, Baton Rouge, LA, "Peripheral Neuro-hormones as a Strategy to Treat Obesity," presented at 2007 CMC Boston—2007 Cardiometabolic Health Congress, Sep. 26-29, 2007, slides 1-35.

Talsania T., et al., "Peripheral exendin-4 and peptide YY(3-36) synergistically reduce food intake through different mechanisms in mice," Endocrinology, Sep. 2005;146(9):3748-56.

Unniappan, S., et al.; "Effects of dipeptidyl peptidase IV on the satiety actions of peptide YY"; Diabetologia; Clinical and Experimental Diabetes and Metabolism; Springer; Berlin, Germany; vol. 49, No. 8; Jun. 27, 2006; pp. 1915-1923.

* cited by examiner

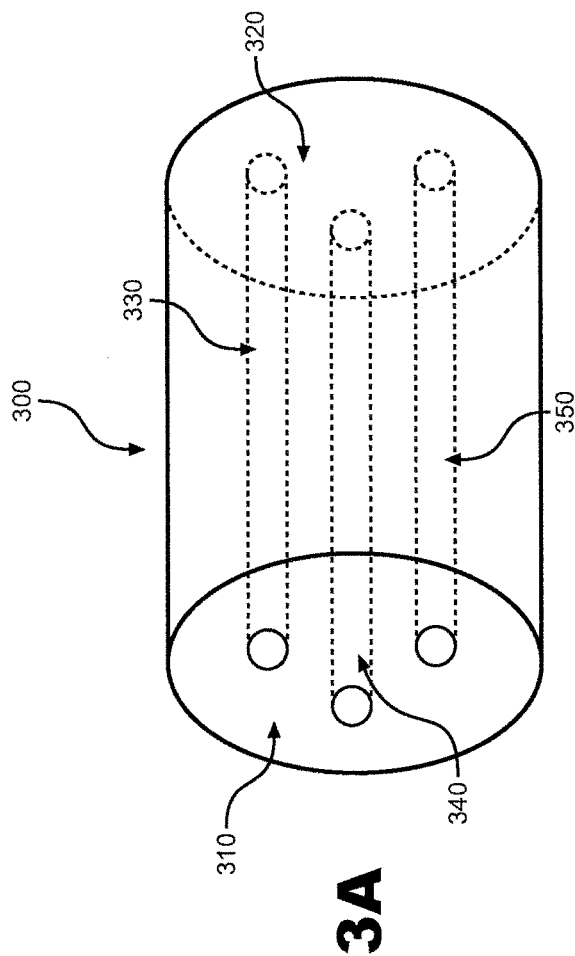
FIG. 3A
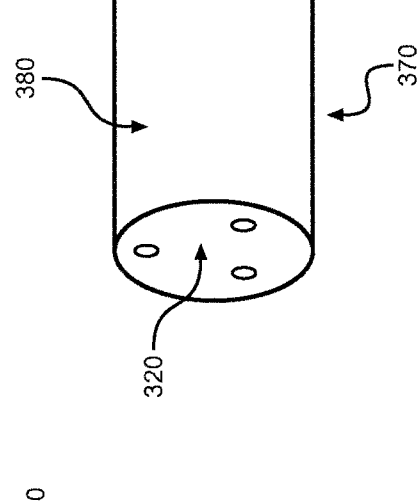
FIG. 3B
FIG. 3C
FIG. 3D

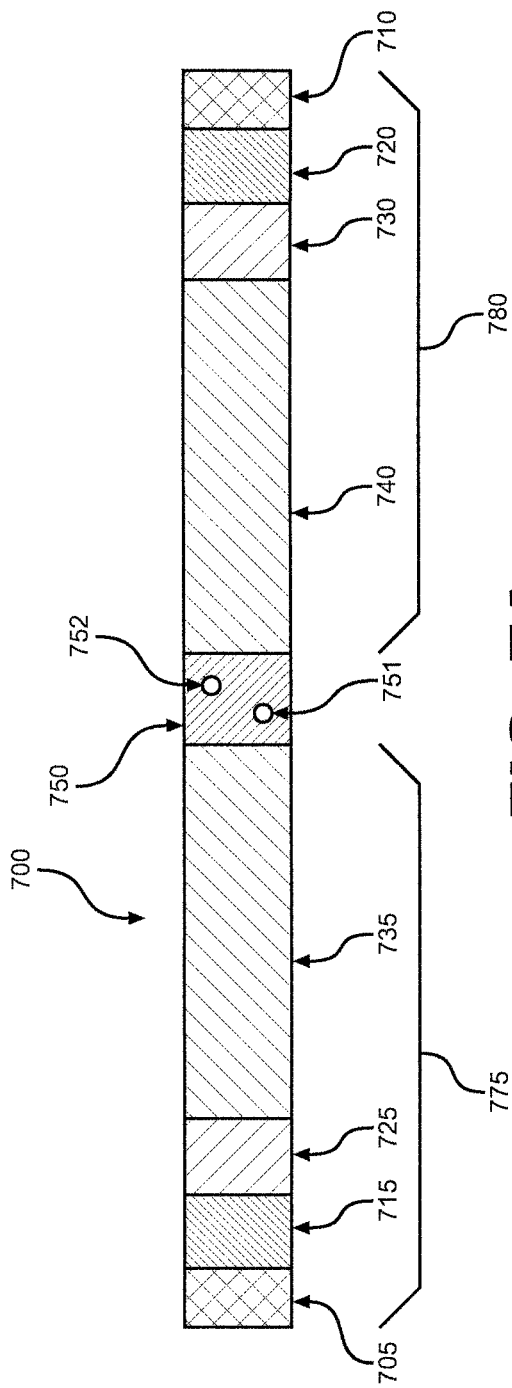
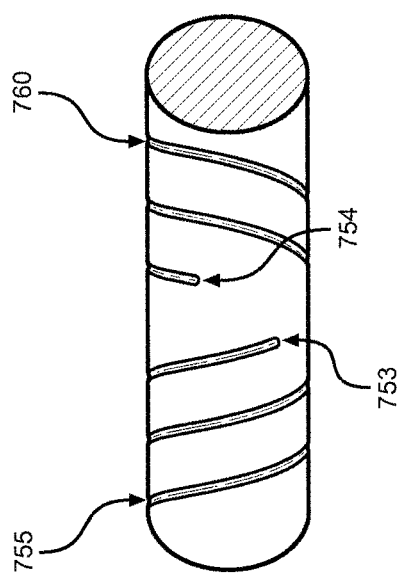

DEVICES, FORMULATIONS, AND METHODS FOR DELIVERY OF MULTIPLE BENEFICIAL AGENTS

CROSS-REFERENCE TO RELATED APPLICATIONS

This application is a divisional of U.S. patent application Ser. No. 12/378,341, filed 12 Feb. 2009, which claims the benefit of U.S. Provisional Application Ser. No. 61/065,692, filed 13 Feb. 2008, which applications are herein incorporated by reference in their entireties.

TECHNICAL FIELD

The present invention relates to devices, formulations, and methods for administration of two or more beneficial agents, for example, for the treatment of one or more disease or condition, wherein the two or more beneficial agents are administered to a subject over a period of time, for example, about two weeks, about four weeks, about six weeks, about eight weeks, about three months, about six months, or up to about a year.

BACKGROUND OF THE INVENTION

Several approaches have been taken for prolonged delivery of a drug at a controlled rate. For example, the NORPLANT® (The Population Council New York, N.Y.) device uses implantable diffusional systems. The NORPLANT® device required the placement of 6 levonorgestrel-filled silastic capsules under the skin (Darney, Current Opinion in Obstetrics and Gynecology 3:470-476 (1991)). Protection from conception for up to five years was achieved. The implants operated by simple diffusion, that is, the drug diffused through a polymeric material at a rate that was controlled by the characteristics of the drug formulation and the polymeric material. Darney describes other biodegradable implants, e.g., the CAPRANOR™ (University of California, San Francisco, Calif.) system and norethindrone pellets. These systems were designed to deliver contraceptives for about one year and then dissolve. The CAPRANOR™ system used poly(ε-caprolactone) capsules filled with levonorgestrel. Norethindrone pellets typically consisted of 10% pure cholesterol with 90% norethindrone.

Implantable infusion pumps have also been described for delivering drugs by intravenous, intraarterial, intrathecal, intraperitoneal, and epidural pathways. Such pumps are typically surgically inserted subcutaneously into a pocket of tissue in the lower abdomen provide for controlled delivery of an drug. A number of systems for insulin delivery, pain management, and chemotherapy delivery have been described (e.g., Health Services/Technology Assessment Text (HSTAT), External and Implantable Infusion Pumps, by Ann A. Graham, C.R.N.A., M.P.H., Thomas V. Holohan, M.D., Health Technology Review, No. 7, Agency for Health Care Policy and Research Office of Health Technology Assessment, January 1994).

Another approach for prolonged delivery of a drug uses osmotic delivery devices. Such a device can be implanted into a subject to release a drug in a controlled manner for a predetermined administration period. In general, these devices operate by imbibing fluid from the outside environment and releasing amounts of the drug corresponding to the imbibed fluid. An example of one such osmotic delivery device is the VIADUR® (Bayer HealthCare Pharmaceuticals, Wayne, N.J.) device. The VIADUR® device is a titanium implant drug-delivery system using DUROS® (ALZA Corporation, Mountain View, Calif.) technology to manage the symptoms associated with advanced (stage 4) prostate cancer by delivering leuprolide acetate. Treatment using the VIADUR® device reduces the amount of testosterone produced and circulated in a subject's body and provides a continuous therapy for 12 months.

The above-described devices and formulations have been useful for delivering drugs to a fluid environment of use. Although these devices have found application for human and veterinary purposes, there remains a need for devices, formulations, and methods of administration that are capable of delivering multiple drugs reliably to a subject at a controlled rate over a prolonged period of time.

SUMMARY OF THE INVENTION

In one aspect, the present invention relates to osmotic delivery devices comprising multiple beneficial agent chambers. Several embodiments are described for dual osmotic delivery devices as well as embodiments of multiple osmotic delivery device, comprising at least two and preferably three or more beneficial agent chambers. Components and examples of materials, from which the components can be made for use in, manufacture of, and assembly of the osmotic delivery devices, are described. Further, components and formulations are provided for osmotic agent formulations and beneficial agent formulations.

In another aspect the present invention relates to combined formulations of beneficial agents. In one embodiment, this aspect of the present invention relates to an osmotic delivery device comprising a beneficial agent chamber containing two or more beneficial agents. The beneficial agent chamber typically contains a beneficial agent formulation comprising two or more beneficial agents and a viscous vehicle. Examples of such beneficial agent formulations include, but are not limited to, the following: (i) two or more beneficial agents dispersed directly in the vehicle; (ii) one or more beneficial agents dispersed directly in the vehicle and one or more beneficial agent formulated into one or more particle formulation that is suspended in the vehicle; (iii) two or more beneficial agents combined in one particle formulation and the particle formulation suspended in the vehicle; and (iv) two or more beneficial agents formulated individually into different particle formulations and the different particle formulations suspended together in the vehicle. The two or more beneficial agents may be, but are not limited to, small molecules, peptides, polypeptides, proteins, polynucleotides (e.g., RNAi molecules), and combinations thereof. Examples of beneficial agents are provided herein.

In another aspect of the present invention relates to osmotic delivery devices loaded with beneficial agent formulations.

In another aspect, the present invention relates to a method of treating a disease or condition in a subject in need of treatment, comprising providing a dual or multiple osmotic delivery device of the present invention to the subject, wherein the osmotic delivery device delivers a therapeutically effective amount of two or more beneficial agents to treat the disease or condition. The dual or multiple osmotic delivery device is implanted in the subject. One or more such dual or multiple osmotic delivery device may be implanted.

In another embodiment, the present invention relates to a method of treating two or more diseases or conditions in a subject in need of treatment, comprising providing a dual or multiple osmotic delivery device of the present invention to the subject, wherein the osmotic delivery device delivers a therapeutically effective amount of (i) one or more beneficial agent to treat a first disease or condition, and (ii) one or more beneficial agent to treat a second disease or condition. The dual or multiple osmotic delivery device is implanted in the subject. One or more such dual or multiple osmotic delivery device may be implanted.

In another aspect the present invention provides a method of treating one or more disease or condition in a subject in need of treatment. In this method, a first osmotic delivery device is provide comprising a first beneficial agent chamber that contains a first beneficial agent formulation, and a second osmotic delivery device is provided comprising a second beneficial agent chamber that contains a second beneficial agent formulation. The first and second beneficial agent formulation each comprises a different beneficial agent, and the first and second device each delivers an amount of beneficial agent to provide effective, therapeutic treatment for the one or more disease or condition. In some embodiments, the first and second beneficial agent both treat the same disease or condition. In other embodiments, the first and second beneficial agents treat different diseases or conditions.

The invention also includes a kit for use in practicing a treatment method of the present invention, wherein the kit provides the osmotic device(s) and may comprise further components as well.

In another aspect the invention includes methods of manufacturing the osmotic delivery devices of the present inventions and kits comprising osmotic delivery devices.

These and other embodiments of the present invention will readily occur to those of ordinary skill in the art in view of the disclosure herein.

BRIEF DESCRIPTION OF THE FIGURES

FIG. 3A illustrates a side view of a multiple channel osmotic delivery device. FIG. 3B illustrates and end view of FIG. 3A. FIG. 3C illustrates and end view of a diffusion moderator component of a multiple channel osmotic delivery device. FIG. 3D illustrates a side view of a diffusion moderator component of a multiple channel osmotic delivery device.

FIG. 7A illustrates a device for dual osmotic delivery that has centrally located diffusion moderators for release of the beneficial agent formulations and distally located semi-permeable membranes for fluid imbibition. FIG. 7B illustrates an example of a single-component diffusion moderator for use with the device.

DETAILED DESCRIPTION OF THE INVENTION

Figure 1:
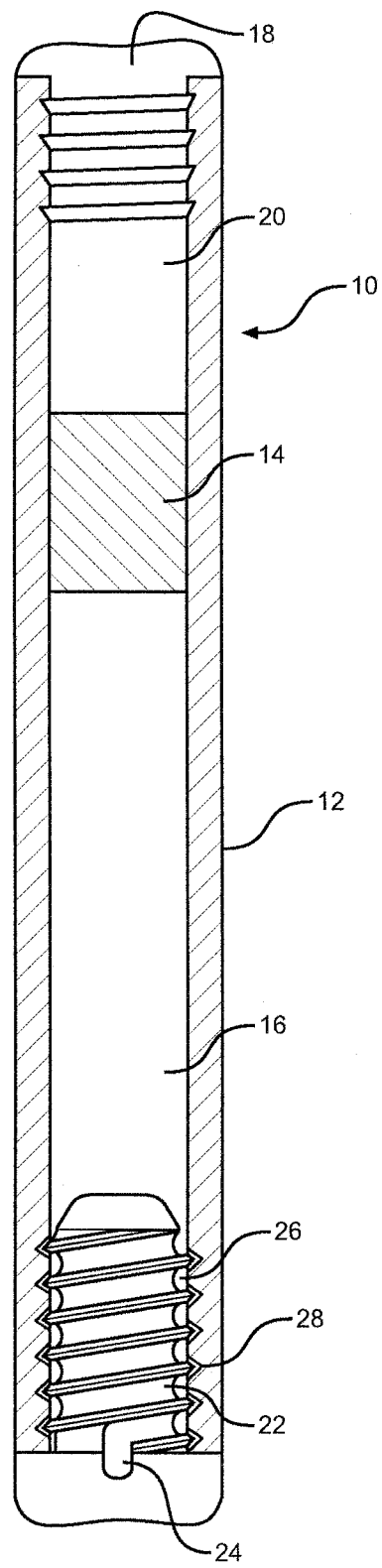
FIG. 1 presents a partial cross-sectional view of one embodiment of an osmotic delivery device useful in the practice of the present invention.

All patents, publications, and patent applications cited in this specification are herein incorporated by reference as if each individual patent, publication, or patent application was specifically and individually indicated to be incorporated by reference in its entirety for all purposes.

The figures illustrating osmotic devices and their components are for illustrative purposes and are not drawn to scale.

1.0 DEFINITIONS

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, mixtures of peptides, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogues, and/or amino acid mimetic). Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl).

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The term "vehicle" as used herein refers to a medium used to carry a compound. Vehicles of the present invention typically comprise components such as polymers and/or solvents. In one embodiment, the vehicle of the present invention is a suspension vehicle. A typical suspension vehicle comprises solvents and polymers in which polypeptide particles are suspended.

The phrase "phase separation" as used herein refers to the formation of multiple phases (e.g., liquid or gel phases) in the vehicle, for example when a suspension vehicle contacts the aqueous environment. In some embodiments of the present invention, a suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound in a vehicle. In one embodiment, a peptide or polypeptide particle is suspended in a suspension vehicle. In another embodiment, a beneficial agent is dissolved in a vehicle or in the same suspension vehicle as a polypeptide particle is suspended.

The phrase "chemically stable" as used herein refers to formation in a formulation of an acceptable percentage of degradation products, including degradation products from the beneficial agents, produced over a defined period of time by chemical pathways, such as deamidation, (usually by hydrolysis), aggregation, oxidation, or reactions with other chemicals.

The phrase "physically stable" as used herein refers to formation in a formulation of an acceptable percentage of aggregates (e.g., dimers and other higher molecular weight products) of beneficial agents. Further, a physically stable formulation does not change its physical state as, for example, from liquid to solid, from amorphous to crystal form, or from one crystal form to another.

The term "viscosity" as used herein typically refers to a value determined from the ratio of shear stress to shear rate (e.g., Considine, D. M. & Considine, G. D., Encyclopedia of Chemistry, 4th Edition, Van Nostrand, Reinhold, N.Y., 1984) essentially as follows:

$$F/A = \mu * V/L \quad \text{(Equation 1)}$$

where

F/A=shear stress (force per unit area), $\mu$=a proportionality constant (viscosity), and V/L=the velocity per layer thickness (shear rate).

From this relationship, the ratio of shear stress to shear rate defines viscosity. Measurements of shear stress and shear rate are typically determined using parallel plate rheometery performed under selected conditions (for example, a temperature of about 37° C.). Other methods for the determination of viscosity include, measurement of a kinematic viscosity using a viscometer, for example, a Cannon-Fenske viscometer, a Ubbelohde viscometer for the Cannon-Fenske opaque solution, or a Ostwald viscometer. Generally, vehicles of the present invention have a viscosity sufficient to prevent a particle formulation or beneficial agent dispersed therein from settling during storage and use in a method of delivery, for example, in an implantable, drug delivery device.

The term "non-aqueous" as used herein refers to an overall moisture content, for example, of a formulation, of a suspension formulation, typically of less than or equal to about 15 wt %, preferably of less than or equal to about 10 wt %, preferably less than or equal to about 7 wt %, more preferably less than or equal to about 5 wt %, and more preferably less than about 4 wt %.

The term "subject" as used herein refers to any member of the subphylum Chordata, including, without limitation, humans and other primates, including non-human primates such as rhesus macaques, cynomolgus monkeys, and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn subjects are included.

The phrase "concurrent delivery" as used herein describes simultaneous, contemporaneous, parallel, or concomitant administration of two or more beneficial agents, wherein the two or more beneficial agents are administered to the same subject over a period of time (e.g., about two weeks, about four weeks, about six weeks, about eight weeks, about three months, about six months, or up to about a year).

The terms "drug," "therapeutic agent," "active agent" and "beneficial agent" are used interchangeably to refer to any therapeutically active substance that is delivered to a subject to produce a desired beneficial effect. In one embodiment of the present invention, the drug is protein, for example, an interferon or an insulinotropic peptide. In another embodiment of the present invention, the drug is a small molecule, for example, steroid hormones such as androgens or estrogens. Examples of numerous beneficial agents are presented herein.

The term "interferon" as used herein includes, but is not limited to, the three major classes of human interferons (e.g., *The Interferons: Characterization and Application*, by Anthony Meager (Editor), Wiley-VCH (May 1, 2006)), as well as analogs, variants, and derivatives thereof, for example: Interferon type I (e.g., alpha interferon (including alfa-2a and alfa-2b), beta interferon (including beta-1a and beta1-b), omega interferon, tau interferon; Interferon type II (e.g., gamma interferon), and Interferon type III (e.g., lambda interferon). Further, the term refers to a variety of consensus interferons (e.g., U.S. Pat. Nos. 4,695,623, 4,897,471, 5,372, 808, 5,541,293, and 6,013,253).

The term "insulinotropic" as used herein refers to the ability of a compound, e.g., a peptide, to stimulate or affect the production and/or activity of insulin (e.g., an insulinotropic hormone). Such compounds typically stimulate the secretion or biosynthesis of insulin in a subject.

The phrase "insulinotropic peptide" as used herein includes, but is not limited to, glucagon-like peptide 1 (GLP-1), as well as analogs, variants, and derivatives thereof, and exendin-4, as well as analogs, variants, and derivatives thereof.

The term "osmotic delivery device" as used herein typically refers to a device used for delivery of one or more beneficial agent to a subject, wherein the device comprises, for example, a reservoir (made, for example, from a titanium alloy) having a lumen that contains, in one chamber, a beneficial agent formulation (e.g., comprising one or more beneficial agent) and, in another chamber, an osmotic agent formulation. A piston assembly positioned in the lumen isolates the beneficial agent formulation from the osmotic agent formulation. A semi-permeable membrane is positioned at a first distal end of the reservoir adjacent the osmotic agent formulation. A diffusion moderator (which defines a delivery orifice through which the beneficial agent formulation exits the device) is positioned at a second distal end of the reservoir adjacent the suspension formulation. The piston assembly and the diffusion moderator define a chamber that contains the beneficial agent formulation and the piston assembly and the semipermeable membrane define a chamber that contains the osmotic agent formulation. The terms "flow modulator," "diffusion modulator," "flow moderator," and "diffusion moderator" are used interchangeably herein. Typically, the osmotic delivery device is implanted within the subject, for example, subcutaneously (e.g., in the inside, outside, or back of the upper arm; or in the abdominal area). An exemplary osmotic delivery device is the DUROS® delivery device.

2.0 GENERAL OVERVIEW OF THE INVENTION

Before describing the present invention in detail, it is to be understood that this invention is not limited to particular beneficial agents, particular types of drug delivery devices, particular sources of beneficial agents, particular solvents, particular polymers, and the like, as use of such particulars may be selected in view of the teachings of the present specification. It is also to be understood that the terminology used herein is for the purpose of describing particular embodiments of the invention only, and is not intended to be limiting. Drawings of the devices are not to scale and are intended to provide schematic representation of the components of the device as well as general spatial relationships.

When describing components, for example, chambers, of an osmotic delivery device, subscripted numbers are typically used to distinguish chambers associated with other components, for example, a first piston that divides a first reservoir into a $first_1$ and a $second_1$ chamber.

In one aspect, the present invention relates to osmotic delivery devices comprising multiple beneficial agent chambers. In one embodiment, the present invention relates to a dual osmotic delivery device. This dual device comprises a first osmotic delivery device contained within a second osmotic delivery device, wherein each osmotic delivery device comprises an impermeable reservoir that defines a lumen and two ends. The diameter of the lumen of the second device is greater than the diameter of the lumen of the first device. The ends of the first and the second device are substantially coincident and each end of the first osmotic delivery device is substantially concentric in relationship to a corresponding end of the second delivery device. The first osmotic delivery device, having an inner and an outer surface, comprises the following components: a first impermeable reservoir; a first piston that divides the first reservoir into a $first_1$ and a $second_1$ chamber and isolates the $first_1$ chamber from the $second_1$ chamber; a first osmotic agent formulation in the $first_1$ chamber; a first beneficial agent formulation in the $second_1$ chamber; a first semi-permeable membrane in sealing relationship with the open end of the $first_1$ chamber; and a first diffusion moderator in mating relationship with the open end of the $second_1$ chamber, wherein the diffusion moderator defines an orifice through which the first beneficial agent is capable of exiting the first device, and the first diffusion moderator effectively isolates the first beneficial agent formulation within the $second_1$ chamber from the environment of use. The second osmotic delivery device, having an inner and an outer surface, comprises the following components: a second piston that divides the second reservoir into a $first_2$ and a $second_2$ chamber, wherein the second piston (i) contacts the inner surface of the second reservoir in sealing relationship, and (ii) defines an internal opening that contacts the outer surface of the first reservoir in sealing relationship, thus isolating the $first_2$ chamber from the $second_2$ chamber; a second osmotic agent formulation in the $first_2$ chamber; a second beneficial agent formulation in the $second_2$ chamber; a second semi-permeable membrane in sealing relationship with the open end of the $second_2$ chamber, wherein the second semi-permeable membrane contacts the outer surface of the first reservoir in sealing relationship; and a second diffusion moderator in mating relationship with the open end of the $second_2$ chamber, wherein (i) the second diffusion moderator (a) defines an orifice through which the second beneficial agent is capable of exiting the device, and (b) contacts the outer surface of the first reservoir in sealing relationship, and (ii) the second diffusion moderator effectively isolates the second beneficial agent formulation within the $second_2$ chamber from the environment of use.

In a second embodiment, the present invention relates to a dual osmotic delivery device, comprising first and second osmotic delivery devices. This dual device comprises an impermeable reservoir having outer and inner surfaces and first and second ends, wherein the reservoir (i) defines a lumen between the first and second ends, and at least one opening between the inner and outer surface, and (ii) the opening is located approximately half-way between the first and second ends. The first osmotic delivery device comprises the following components: a first reservoir portion extending from the first end of the reservoir to adjacent the opening; a first piston that divides the first reservoir portion into a $first_1$ and a $second_1$ chamber, and isolates the $first_1$ chamber from the $second_1$ chamber, wherein the $first_1$ chamber is adjacent the opening; a first osmotic agent formulation in the $first_1$ chamber; a first beneficial agent formulation in the $second_1$ chamber; a first semi-permeable membrane in sealing relationship with the open end of the $first_1$ chamber, wherein the first semi-permeable membrane is adjacent the opening and isolates the $first_1$ chamber from the opening; and a first diffusion moderator in mating relationship with the open end of the $second_1$ chamber, wherein (i) the diffusion moderator defines an orifice through which the first beneficial agent is capable of exiting the $second_1$ chamber, and (ii) the first diffusion moderator effectively isolates the first beneficial agent formulation within the $second_1$ chamber from the environment of use. The second osmotic delivery device comprises the following components: a second reservoir portion extending from the second end of the reservoir to adjacent the opening; a second piston that divides the second reservoir portion into a $first_2$ and a $second_2$ chamber, and isolates the $first_2$ chamber from the $second_2$ chamber, wherein the $first_2$ chamber is adjacent the opening; a second osmotic agent formulation in the $first_2$ chamber; a second beneficial agent formulation in the $second_2$ chamber; a second semi-permeable membrane in sealing relationship with the open end of the $first_2$ chamber, wherein the second semi-permeable membrane is adjacent the opening and isolates the $first_2$ chamber from the opening; and a second diffusion moderator in mating relationship with the open end of the $second_2$ chamber, wherein the diffusion moderator defines an orifice through which the second beneficial agent is capable of exiting the $second_2$ chamber, wherein the second diffusion moderator effectively isolates the second beneficial agent formulation within the $second_2$ chamber from the environment of use. In this dual device the first semi-permeable membrane and the second semi-permeable membrane define a fluid imbibition chamber that includes a portion of the reservoir that defines the opening.

In a third embodiment, the present invention relates to a dual osmotic delivery device, comprising first and second osmotic delivery devices. This dual device comprises an impermeable reservoir having outer and inner surfaces and first and second ends, wherein the reservoir (i) defines a lumen between the first and second ends, (ii) defines at least two openings between the inner and outer surface, and (iii) the openings are located approximately half-way between the first and second ends. The first device comprises the following components: a first reservoir portion extending from the first end of the reservoir to adjacent the openings; a first piston that divides the first reservoir portion into a $first_1$ and a $second_1$ chamber, wherein the piston isolates the $first_1$ chamber from the $second_1$ chamber, and the $second_1$ chamber is adjacent the openings; a first osmotic agent formulation in the $first_1$ chamber; a first beneficial agent formulation in the $second_1$ chamber; a first semi-permeable membrane in sealing relationship with the open end of the $first_1$ chamber; and a first diffusion moderator in mating relationship with the open end of the $second_1$ chamber, wherein the diffusion moderator defines an orifice through which the first beneficial agent is capable of exiting the $second_1$ chamber, the orifice is aligned with one of the openings in the reservoir, and the first diffusion moderator effectively isolates the first beneficial agent formulation within the $second_1$ chamber from the environment of use. The second osmotic delivery device comprises the following components: a second reservoir portion extending from the second end of the reservoir to adjacent the openings; a second piston that divides the second reservoir portion into a $first_2$ and a $second_2$ chamber, wherein the piston isolates the $first_2$ chamber from the $second_2$ chamber, and the $second_2$ chamber is adjacent the openings; a second osmotic agent formulation in the $first_2$ chamber; a second beneficial agent formulation in the $second_2$ chamber; a second semi-permeable membrane in sealing relationship with the open end of the $first_2$ chamber; and a second diffusion moderator in mating relationship with the open end of the $second_2$ chamber, wherein the diffusion moderator defines an orifice through which the second beneficial agent is capable of exiting the $second_2$ chamber, the orifice is aligned with the second opening in the reservoir, and the diffusion moderator effectively isolates the second beneficial agent formulation within the $second_2$ chamber from the environment of use.

In a fourth embodiment, the present invention relates to a dual osmotic delivery device, comprising first and second osmotic delivery devices. The first osmotic delivery device comprises the following components: a first impermeable reservoir having a first open end and a second open end; a first piston that divides the first reservoir into a $first_1$ and a $second_1$ chamber, wherein the piston isolates the $first_1$ chamber from the $second_1$ chamber; a first osmotic agent formulation in the $first_1$ chamber; a first beneficial agent formulation in the $second_1$ chamber; a first semi-permeable membrane in sealing relationship with the open end of the $first_1$ chamber; and a diffusion moderator in mating relationship with the open end of the $second_1$ chamber, wherein the diffusion moderator defines a first orifice through which the first beneficial agent is capable of exiting the $second_1$ chamber, and the diffusion moderator effectively isolates the first beneficial agent formulation within the $second_1$ chamber from the environment of use. The second osmotic delivery device comprises the following components: a second impermeable reservoir having a first open end and a second open end; a second piston that divides the second reservoir portion into a $first_2$ and a $second_2$ chamber, wherein the piston isolates the $first_2$ chamber from the $second_2$ chamber; a second osmotic agent formulation in the $first_2$ chamber; a second beneficial agent formulation in the $second_2$ chamber; and a second semi-permeable membrane in sealing relationship with the open end of the $first_2$ chamber. In this embodiment, the diffusion moderator is in mating relationship with the open end of the $second_2$ chamber, wherein the diffusion moderator defines a second orifice through which the second beneficial agent is capable of exiting the $second_2$ chamber, and the diffusion moderator effectively isolates the second beneficial agent formulation within the $second_2$ chamber from the environment of use.

In a fifth embodiment, the present invention relates to a dual osmotic delivery device, comprising an impermeable reservoir having outer and inner surfaces and first and second ends, wherein the reservoir defines a first chamber adjacent the first end of the reservoir in fluid communication with second and third essentially columnar chambers that extend to the second end of the reservoir each of the second and third chambers defining an open end, wherein each set of the first chamber and second chamber, and the first chamber and the third chamber defines a flow path through the reservoir. A first piston and a second piston are located in the second and third chambers, respectively, wherein the pistons isolate the first chamber from the second and third chambers. An osmotic agent formulation is present in the first chamber. A semi-permeable membrane is positioned in sealing relationship with the open end of the first chamber. A first beneficial agent formulation is present in the second chamber, and a second beneficial agent formulation in the third chamber. A diffusion moderator is positioned in mating relationship with the end of the reservoir, wherein the diffusion moderator defines a first orifice through which the first beneficial agent is capable of exiting the second chamber, and a second orifice through which the second beneficial agent is capable of exiting the third chamber. The diffusion moderator effectively isolates the first and second beneficial agent formulations, within, respectively, the second and third chambers, from the environment of use.

In a sixth embodiment, the present invention relates to a multiple osmotic delivery device, comprising at least two and preferably three or more beneficial agent chambers. In one embodiment, this multiple osmotic delivery device comprises three beneficial agent chambers. This multiple osmotic delivery device comprises an impermeable reservoir having first and second ends, wherein the reservoir defines at least first, second and third essentially columnar hollow tubes that extend from the first end of the reservoir to the second end of the reservoir, each of the first, second and third essentially columnar hollow tube defining a first open end and a second open end. The first osmotic delivery device comprises the following components: a first piston that divides the first columnar tube into a $first_1$ and a $second_1$ chamber, wherein the piston isolates the $first_1$ and $second_1$ chambers; a first osmotic agent formulation in the $first_1$ chamber; a first beneficial agent formulation in the $second_1$ chamber; a first semi-permeable membrane in sealing relationship with the first open end of the $first_1$ chamber; and a diffusion moderator in mating relationship with the second open end of the $second_1$ chamber, wherein the diffusion moderator defines an orifice through which the first beneficial agent is capable of exiting the $second_1$ chamber, and the diffusion moderator effectively isolates the first beneficial agent formulation within the $second_1$ chamber from the environment of use. The second osmotic delivery device comprises the following components: a second piston that divides the second columnar tube into a $first_2$ and a $second_2$ chamber, wherein the piston isolates the $first_2$ and $second_2$ chambers; a second osmotic agent formulation in the $first_2$ chamber; a second beneficial agent formulation in the second$_2$ chamber; a second semi-permeable membrane in sealing relationship with the first open end of the first$_2$ chamber; and a diffusion moderator in mating relationship with the second open end of the second$_2$ chamber, wherein the diffusion moderator defines an orifice through which the second beneficial agent is capable of exiting the second$_2$ chamber, and the diffusion moderator effectively isolates the second beneficial agent formulation within the second$_2$ chamber from the environment of use. The third osmotic delivery device comprises the following components: a third piston that divides the third columnar tube into a first$_3$ and a second$_3$ chamber, wherein the piston isolates the first$_3$ and second$_3$ chambers; a third osmotic agent formulation in the first$_3$ chamber; a third beneficial agent formulation in the second$_3$ chamber; a third semi-permeable membrane in sealing relationship with the first open end of the first$_3$ chamber; and a diffusion moderator in mating relationship with the second open end of the second$_3$ chamber, wherein the diffusion moderator defines an orifice through which the third beneficial agent is capable of exiting the second$_3$ chamber, and the diffusion moderator effectively isolates the third beneficial agent formulation within the second$_3$ chamber from the environment of use.

The reservoir of the osmotic delivery devices of the present invention can be made of number of substantially impermeable materials. In preferred embodiments, the reservoir is made of titanium or a titanium alloy.

In the osmotic delivery systems of the present invention, the osmotic agent formulation may be the same in all osmotic formulation chambers or different formulations may be used in different chambers.

In some embodiments, each beneficial agent chamber contains a beneficial agent formulation comprising a single beneficial agent and a vehicle, typically a viscous vehicle. In other embodiments of the present invention, at least one beneficial agent chamber contains a beneficial agent formulation comprising two or more beneficial agents and a vehicle, typically a viscous vehicle. When the beneficial agent formulation comprises two or more beneficial agents and a viscous vehicle, examples of combined formulations include, but are not limited to, the following: (i) two or more beneficial agents dispersed directly in the vehicle; (ii) one or more beneficial agent dispersed directly in the vehicle and one or more beneficial agent formulated into a particle formulation that is suspended in the vehicle; (iii) two or more beneficial agents combined in one particle formulation and the particle formulation suspended in the vehicle; and (iv) two or more beneficial agents formulated individually into different particle formulations and the different particle formulations suspended together in the vehicle.

In another aspect the present invention relates to combined beneficial agent formulations. Examples of such beneficial agent formulations include, but are not limited to, the following: (i) two or more beneficial agents dispersed directly in the vehicle; (ii) one or more beneficial agent dispersed directly in the vehicle and one or more beneficial agent formulated into a particle formulation that is suspended in the vehicle; (iii) two or more beneficial agents combined in one particle formulation and the particle formulation suspended in the vehicle; and (iv) two or more beneficial agents formulated individually into different particle formulations and the different particle formulations suspended together in the vehicle. In one embodiment, this aspect of the present invention relates to an osmotic delivery device comprising a beneficial agent chamber containing two or more beneficial agents. The beneficial agent chamber typically contains a beneficial agent formulation comprising two or more beneficial agents and a viscous vehicle.

In some embodiments of the combined beneficial agent formulations of the present invention, at least one beneficial agent is a small molecule and at least one beneficial agent is a polypeptide, in other embodiments at least two beneficial agents are polypeptides, and in other embodiments at least two beneficial agents are small molecules. When the combined beneficial agent formulation comprises at least two polypeptides, the formulation may comprise the polypeptides in a variety of ways, including, but not limited to, the following: at least one of the polypeptides may be dissolved in the vehicle; at least one of the polypeptides may be formulated into a particle formulation that is suspended in the vehicle; at least two polypeptides may be formulated into one particle formulation that is suspended in the vehicle; a first polypeptide may be formulated into a first particle formulation and a second polypeptide may be formulated into a second particle formulation, and the first and second particle formulations are suspended in the vehicle (and so on for additional proteins); and combinations thereof.

In one embodiment of the present invention, a first polypeptide is exendin-4, a second polypeptide is oxyntomodulin or PYY, wherein two of the polypeptides are formulated into one particle formulation or the polypeptides are separately formulated into individual particle formulations (e.g., Examples 1-4). In another embodiment of the present invention, a first particle formulation comprises one or more polypeptide (e.g., interferon) and a second formulation comprises a small molecule (e.g., Amphotericin B) in a formulation (e.g., suspension formulation or solution formulation). In another embodiment of the present invention, a first polypeptide is amylin and a second polypeptide is leptin, wherein the polypeptides are both formulated into one particle formulation or the polypeptides are separately formulated into individual particle formulations (e.g., one particle formulation comprising amylin and a second particle formulation comprising leptin).

In another aspect, the present invention relates to a method of treating a disease or condition in a subject in need of treatment, comprising providing a dual or multiple osmotic delivery device of the present invention to the subject, wherein the osmotic delivery device delivers a therapeutically effective amount of two or more beneficial agents to treat the disease or condition. The dual or multiple osmotic delivery device is implanted in the subject. One or more such dual or multiple osmotic delivery device may be implanted.

In another embodiment, the present invention relates to a method of treating two or more diseases or conditions in a subject in need of treatment, comprising providing a dual or multiple osmotic delivery device of the present invention to the subject, wherein the osmotic delivery device delivers a therapeutically effective amount of (i) one or more beneficial agent to treat a first disease or condition, and (ii) one or more beneficial agent to treat a second disease or condition. The dual or multiple osmotic delivery device is implanted in the subject. One or more such dual or multiple osmotic delivery device may be implanted.

In another aspect the present invention provides a method of treating one or more disease or condition in a subject in need of treatment. In this method a first osmotic delivery device is provide comprising a first beneficial agent chamber that contains a first beneficial agent formulation, and a second osmotic delivery device is provided comprising a second beneficial agent chamber that contains a second beneficial agent formulation. The first and second beneficial agent formulation each comprises a different beneficial agent, and the first and second device each delivers an amount of beneficial agent to provide effective, therapeutic treatment for the one or more disease or condition. In some embodiments, the first and second beneficial agent both treat the same disease or condition. In some embodiments of the present invention, the first beneficial agent is exendin-4, the second beneficial agent is oxyntomodulin or PYY, and the method of treating facilitates or promotes weight loss. In another embodiment of the present invention, the first beneficial agent is exendin-4, the second beneficial agent is oxyntomodulin, and the third beneficial agent is PYY, and the method of treating facilitates or promotes weight loss. In another embodiment of the present invention, the first beneficial agent is amylin, the second beneficial agent is leptin, and the method of treating facilitates or promotes weight loss. In other embodiments, the first and second beneficial agents treat different diseases or conditions.

The invention also includes a kit for use in practicing a treatment method of the present invention, wherein the kit provides the osmotic device(s) and may comprise further components as well. In one embodiment, the kit of the present invention provides at least a first osmotic delivery device, comprising a first beneficial agent chamber that contains a first beneficial agent formulation, and a second osmotic delivery device, comprising a second beneficial agent chamber that contains a second beneficial agent formulation, wherein the first and second beneficial agent formulation each comprises a different beneficial agent.

The present invention also includes methods of manufacturing the osmotic delivery devices and kits of the present invention. Methods of manufacturing typically include positioning and assembling the components of the osmotic delivery devices into functional relationship, as well as assembly of the components of the kit. Kits are typically sterile and may be sterilized and kept sterile by a variety of means known in the art.

These aspects and embodiments of the invention are described in detail with reference to some preferred embodiments, as illustrated, for example, in the accompanying drawings. In describing some preferred embodiments herein below, numerous specific details are set forth in order to provide a thorough understanding of the invention. However, it will be apparent to one skilled in the art that the invention may be practiced without some or all of these specific details. In other instances, well-known features and/or process steps have not been described in detail so as not to unnecessarily obscure the invention. In addition, like or identical reference numerals are used to identify common or similar elements.

2.1 Devices for Use in the Practice of the Present Invention

In one aspect, the present invention relates to the use of osmotic delivery devices for the delivery of two or more beneficial agents. In some embodiments, two or more delivery devices are used wherein the devices are typically implanted at one or more location in the body of a subject. In other embodiments, a single device is used for the delivery of multiple beneficial agent formulations, wherein the device is implanted at a single location within the body of a subject.

Some osmotic delivery devices and their component parts have been described, for example, the DUROS® delivery device or similar devices (e.g., U.S. Pat. Nos. 5,609,885, 5,728,396, 5,985,305, 5,997,527, 6,113,938, 6,132,420, 6,156,331, 6,217,906, 6,261,584, 6,270,787, 6,287,295, 6,375,978, 6,395,292, 6,508,808, 6,524,305, 6,544,252, 6,635,268, 6,682,522, 6,923,800, 6,939,556, 6,976,981, 6,997,922, 7,014,636, 7,074,423, 7,207,982, 7,112,335, 7,163,688, 7,241,457; U.S. Patent Publication Nos. 2005-0175701, 2007-0281024, 2008-0091176).

The DUROS® device releases an beneficial agent at a predetermined rate based on the principle of osmosis. Extracellular fluid (e.g., from the fluid environment into which the device was placed, for example, by implantation in a subject) enters the DUROS® device through a semi-permeable membrane directly into an osmotic engine (e.g., a chamber comprising an osmotic agent formulation) that expands to drive the piston at a slow and even delivery rate. Movement of the piston forces the beneficial agent formulation to be released through the orifice or exit port.

Implantable devices, for example, the DUROS® device, provide the following advantages for administration of a beneficial agent formulations: true zero-order release of the beneficial agent pharmacokinetically; long-term release period time (e.g., up to about a year); and reliable delivery and dosing of a beneficial agent.

FIG. 1 depicts an example of an osmotic delivery system useful in the practice of the present invention. In FIG. 1, an osmotic delivery device 10 is shown comprising a reservoir 12. A piston assembly 14 is positioned in the lumen of the reservoir and divides the lumen into two chambers. In this example, the chamber 16 contains a beneficial agent formulation and the chamber 20 contains an osmotic agent formulation. A semi-permeable membrane 18 is positioned at a distal end of the reservoir, adjacent the chamber 20 containing the osmotic agent formulation. A diffusion moderator 22 is positioned in mating relationship at a distal end of the reservoir 12, adjacent the chamber 16 containing the beneficial agent formulation. The diffusion moderator 22 includes a delivery orifice 24. The diffusion moderator 22 may be any suitable flow device having a delivery orifice. In this embodiment, the flow path 26 is formed between a threaded diffusion moderator 22 and threads 28 formed on the interior surface of the reservoir 12. In alternative embodiments, the diffusion moderator can, for example, (i) be press-fit (or friction fit) through an opening and contacting a smooth interior surface of the reservoir, or (ii) comprise two pieces with an outer shell constructed and arranged for positioning in an opening, an inner core inserted in the outer shell, and a fluid channel having a spiral shape defined between the outer shell and the inner core (e.g., U.S. Patent Publication No. 2007-0281024).

Fluid is imbibed into the chamber 20 through the semi-permeable membrane 18. The beneficial agent formulation is dispensed from the chamber 16 through the delivery orifice 24 in the diffusion moderator 22. The piston assembly 14 engages and seals against the interior wall of the reservoir 12, thereby isolating the osmotic agent formulation in chamber 20 and fluid imbibed through the semi-permeable membrane 18 from the beneficial agent formulation in chamber 16. At steady-state, the beneficial agent formulation is expelled through the delivery orifice 24 in the diffusion moderator 22 at a rate corresponding to the rate at which external fluid is imbibed into the chamber 20 through the semi-permeable membrane 18.

The semi-permeable membrane 18 may be in the form of a plug that is resiliently engaged in sealing relationship with the interior surface of the reservoir 12. In FIG. 1, it is shown to have ridges that serve to frictionally engage the semi-permeable membrane 18 with the interior surface of the reservoir 12.

In view of the teachings of the present specification, one of ordinary skill in the art can select the appropriate number and type of osmotic delivery devices for use in the methods of the present invention.

2.1.1 Devices Comprising a Single Beneficial Agent Formulation Chamber

In one embodiment of the present invention, two or more osmotic delivery devices, each having a single beneficial agent chamber (e.g., as shown in FIG. 1), are implanted in a subject at one or more locations. For example, two delivery devices are implanted in a subject, the first device containing a formulation comprising a first beneficial agent, and a second device containing a formulation comprising a second beneficial agent. For example, one device may be implanted subcutaneously in the upper left arm and the second device implanted subcutaneously in the upper right arm, or one device may be implanted subcutaneously in the lower left abdomen and the second device implanted subcutaneously in the lower right abdomen.

Examples of formulations and beneficial agents are discussed herein below. Two or more osmotic delivery devices, each having a single beneficial agent chamber, may comprise the same or different beneficial agent in a formulation to achieve, for example, delivery of the same beneficial agent for different duration (i.e., different periods of time), or to achieve differential dosing over time, for example, a step-down dosing (e.g., wherein the beneficial agent in a first device is depleted before the beneficial agent in the second device), or a step-up dosing (e.g., wherein the first device delivers the beneficial agent over a period of time and the second device begins delivery of the beneficial agent at a later time than the first device or is implanted at a later time). Step-down and step-up dosing methods are discussed further herein below. Further, two or more osmotic delivery devices having single beneficial agent chambers may be used to deliver two or more different beneficial agents, wherein the two or more beneficial agents are used for the treatment of one or more disease or condition. For example, a first osmotic delivery device, comprising exendin-4, and a second delivery device, comprising a oxyntomodulin or PYY, can both be implanted in a subject to facilitate or promote weight loss, for example, in obese or overweight subjects. As another example, a first osmotic delivery device, comprising amylin, and a second delivery device, comprising a leptin, can both be implanted in a subject to facilitate or promote weight loss, for example, in obese or overweight subjects.

Two or more osmotic delivery devices comprising two or more different beneficial agents may be provided in a kit for the treatment of one or more disease or condition. Further, the kit may include one or more of the following: instructions; a topical anesthetic (e.g., 10 ml ampule 2% lidocaine); assorted surgical tools and accessories (e.g., forceps, hemostat clamp, surgical drape(s), povidone iodine swab(s), syringe(s), needle(s), surgical blade(s) and handle, gauze sponge(s), skin protectant, wound closure strip(s), adhesive bandage(s), alcohol pad(s), marking pen, and ruler); and an implantor device (e.g., U.S. Pat. No. 6,190,350).

In a second embodiment of the present invention, a single osmotic delivery device having a single beneficial agent chamber is implanted in a subject, wherein the single device contains a formulation comprising two or more beneficial agents. Examples of such formulations are described further herein below ("Combined Formulations").

In a third embodiment of the present invention, a single osmotic delivery device having a single beneficial agent chamber is implanted in the subject, wherein two or more beneficial agent formulations are alternately layered within the beneficial agent chamber of the osmotic delivery device such that delivery of each beneficial agent occurs for a period of time followed by delivery of the second beneficial agent, etc., creating a cycle of delivery of the beneficial agents. This results in stratified layers of beneficial agents within the beneficial agent chamber. As the beneficial agent formulations are delivered a steady-state level of each agent is established over time with peak doses (i.e., Cmax) of the beneficial agents separated over time. Such a delivery profile is schematically represented in FIG. 2.

The layers of beneficial agent formulations remain discrete by virtue of viscous nature of the vehicle in which the beneficial agents are formulated.

Figure 2:
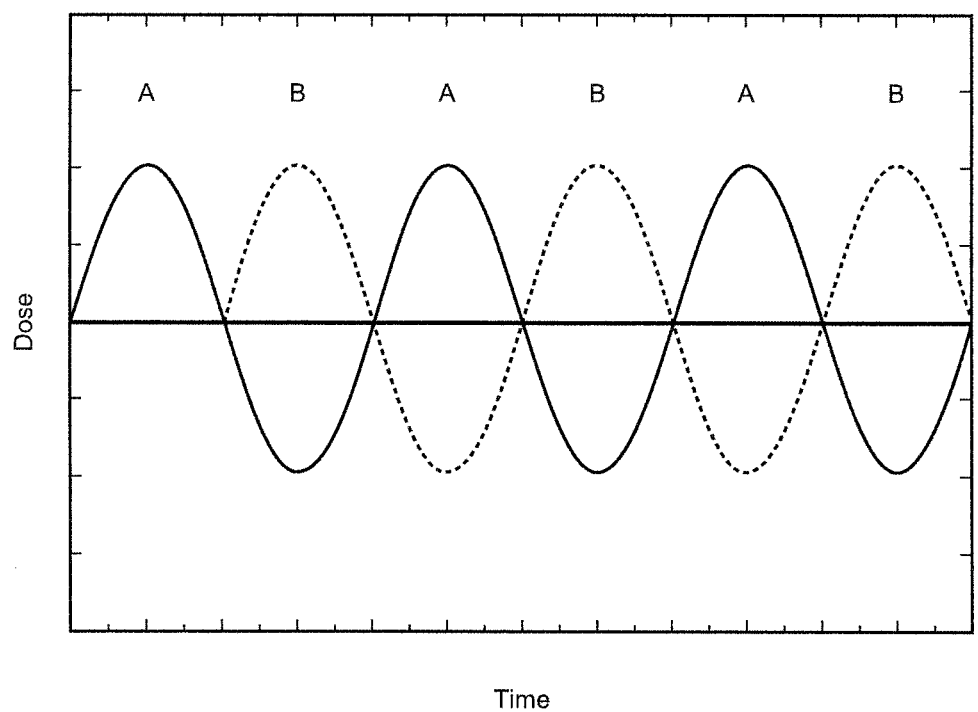
FIG. 2 presents a schematic diagram representing the delivery of two, layered beneficial agent formulations from a single osmotic delivery device. The dose or amount of the beneficial agent being delivered in shown on the Y axis and the time period over which the beneficial agents are delivered is shown on the X axis.

In FIG. 2, beneficial agents A (curve shown as a solid line) and B (curve shown as a dashed line) are delivered sequentially. The top of the curve for each of agents A and B represents the Cmax. The straight line across the center of the graph represents the average steady state delivery dose of the two beneficial agents. The amplitude of each curve is related to the amount of beneficial agent being delivered, the rate at which the beneficial agent formulation is delivered, and the thickness of the layer of the beneficial agent in the osmotic device.

An example of the usefulness of this approach to delivery of multiple beneficial agents is alternating delivery of two polypeptides when co-administration of the two polypeptides can produce toxic effects. For example, administration of an interferon with a cytokine (e.g., IL-2), where the alternating delivery maintains therapeutic levels of the two polypeptides but abates the toxic effects of the two polypeptides being co-administered.

2.1.2 Devices Comprising Multiple Beneficial Agent Chambers

The osmotic delivery devices of the present invention having multiple beneficial agent chambers typically deliver one beneficial agent formulation per delivery orifice. However, use of the combined formulations described herein below expand the usefulness of the osmotic delivery devices having multiple delivery orifices in terms of the number of beneficial agents that can be delivered from any given device. Thus, although the devices described herein are exemplified for use with two different beneficial agents, use of the combined formulations described herein in these devices is also an aspect of the present invention.

Further, each beneficial agent chamber of osmotic delivery devices comprising two or more beneficial agent chambers (as described herein) can be used in similar ways as described above for delivery of beneficial agent from osmotic delivery devices having a single beneficial agent chamber (e.g., two or more devices, or stratification of beneficial agent formulations), thus further expanding the uses of the devices comprising two or more beneficial agent chambers.

2.1.2.1 Multiple Channel Devices

In one embodiment of the present invention, a cylindrical tube is made (e.g., by boring a solid material such as titanium or a titanium alloy) to create multiple channels, for example, a three channel tube (FIG. 3A). Each channel of the tube is then adapted with the above-described components of the osmotic device, including, for each channel, a semi-permeable membrane, an osmotic agent chamber, a piston, a beneficial agent chamber, a diffusion moderator, and an orifice. Each the beneficial agent formulation in each channel can comprise a different beneficial agent, or, in some embodiments, multiple channels may contain the same beneficial agent at the same or different dosage amounts or concentrations.

In FIG. 3A, an example of a three-channel reservoir 300 is illustrated. The first distal end of the tube 310 comprises three openings that are adapted to receive the semi-permeable membranes, each of the three channels 330, 340, 350 comprises an osmotic agent chamber, a piston, and a beneficial agent chamber. The second distal end of the tube 320 comprises three openings that are adapted to receive diffusion moderators that each comprises an orifice.

Typically all of the diffusion moderators are located at the same distal end of device and all of the semi-permeable membranes are located at the opposite distal end of the device. In other embodiments, the orifice for each channel's diffusion moderator may be on the outer, side surface of the device near a distal end. Combinations of such locations for the diffusion moderator orifices can also be made.

Such devices may further comprise a cap-like structure (FIG. 3D, 370) at the end of the device where the orifices of the diffusion moderators are located such that the cap creates a terminal diffusion moderator defining a single exit orifice from the device when the cap-like structure is in operative contact with the device. That is, the end of the device where the orifices of the diffusion moderators are located creates an inner diffusion moderator surface (FIG. 3A, FIG. 3B, FIG. 3D, 320), which is adjacent to a chamber (FIG. 3D, 380) into which the beneficial agent formulations exit the device, which is adjacent to an outer diffusion moderator surface (FIG. 3C, FIG. 3D, 360) comprising a single orifice (FIG. 3C, FIG. 3D, 390) through which the mixture of beneficial agents exits the cap-like structure. Typically such a cap is positioned in mating relationship with the device and held in place by, for example, press-fit (i.e., interference fit) or complementary continuous helical threads/grooves. Alternatively, such a cap may be an integral part of the overall structure of the reservoir. Means for holding cap in place (e.g., friction fit or thread and groove) are not shown in FIG. 3D.

Although this example is described with reference to three channels, a similar two-channel device can be made as well as a similar device having more than three channels. Devices of this type have the advantage of being a single implantable device useful for the delivery of, for example, multiple beneficial agent formulations in the same vehicle as well as multiple beneficial agent formulations in different vehicles.

Further, such devices have the advantage of being adapted to provide different flow rates for delivery of the beneficial agent formulations in the different channels by, for example, using different semi-permeable material in one or more of the channels that each provide different rates of fluid imbibition into the osmotic agent chamber. In addition, osmotic agent formulations having different expansion properties can be employed. For example, the osmotic agent formulation may include one or more osmotic polymers. An osmotic polymer is a hydrophilic polymer that can imbibe aqueous fluids (such as biological fluids and water) and upon imbibing aqueous fluids expands to an equilibrium state and retains a significant portion of the imbibed fluid. Depending on the osmotic polymer that is selected, the polymer can expand to varying degrees, for example, about 2 to about 50 times its initial volume. An osmotic polymer may or may not be cross-linked. Preferred osmotic polymers are hydrophilic polymers that are lightly cross-linked, such cross-links being formed by covalent or ionic bonds or residue crystalline regions after swelling. Osmotic polymers may be, for example, of plant, animal or synthetic origin.

In an alternative embodiment, an osmotic delivery device is formed having a single semi-permeable membrane, a single osmotic agent chamber, multiple channels in fluid communication with the osmotic agent chamber, a piston assembly in each channel, a beneficial agent chamber in each channel, and at least one diffusion moderator that defines a flow path from each beneficial agent chamber to an exit orifice. An illustration of such an embodiment is presented in FIG. 4A and FIG. 4B.

Figure 4A:
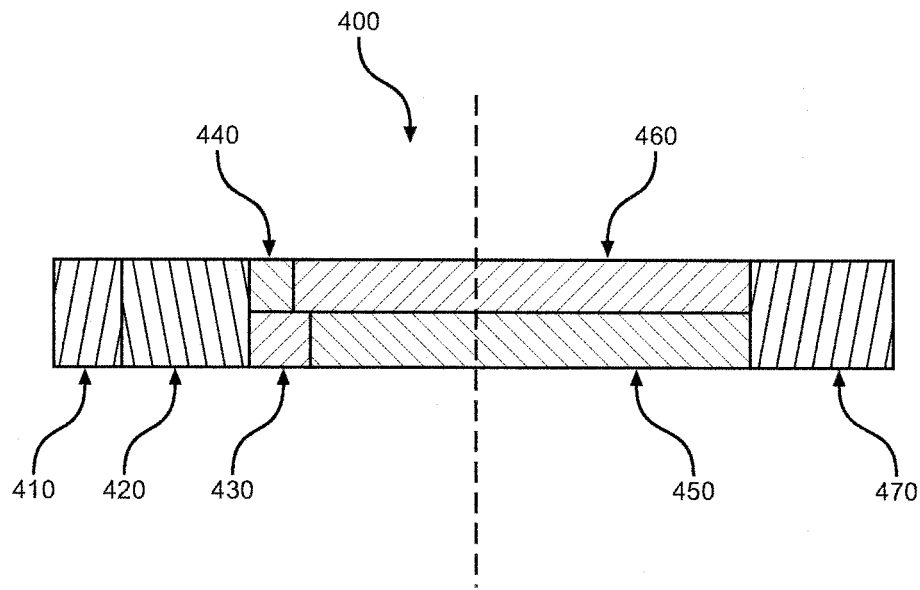
FIG. 4A illustrates a side view osmotic delivery device comprising two channels.

FIG. 4A illustrates an osmotic delivery device (FIG. 4A, 400) comprising two channels. A semi-permeable membrane 410 is adjacent an osmotic agent chamber 420 which is in fluid communication with two channels. In each channel, a piston assembly 430, 440 is placed to isolate the beneficial agent chamber 450, 460 from the osmotic agent chamber 420. At the distal end of channels is a diffusion moderator 470 that forms a flow path from each beneficial agent chamber to one or more orifice through which the beneficial agent formulation will exit the device. The flow paths may, for example, (i) merge to a single flow path to a single orifice, (ii) flow into a cap-like structure as discussed herein above that results in a single exit orifice from the device (e.g., FIG. 3D), or (iii) each define a flow path from a single beneficial agent chamber to an orifice (thus providing two orifices from which the beneficial agent formulations exit the device, one formulation from each orifice).

Figure 4B:
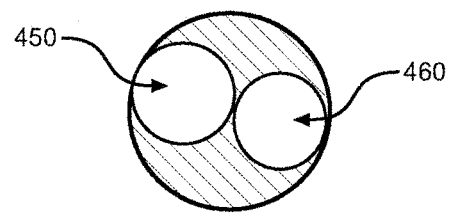
FIG. 4B illustrates the relationship of the two channels within a larger diameter columnar structure and shows a cross sectional area at the dashed line of FIG. 4A.

FIG. 4B illustrates the relationship of the two channels 450, 460 within a larger diameter columnar structure. FIG. 4B shows a cross sectional area at the dashed line of FIG. 4A. The two channels may, for example, be bored through solid columnar structure (e.g., made from a suitable reservoir material, such as titanium or a titanium alloy).

Advantages of this type of device include being a single implantable device useful for the delivery of, for example, multiple beneficial agent formulations in the same vehicle as well as multiple beneficial agent formulations in different vehicles, wherein the delivery rate of the beneficial agent formulations is determined based on a fluid imbibition rate of a single semi-permeable membrane and expansion property of a single osmotic agent formulation.

2.1.2.2 Grouped Devices

In another embodiment of the present invention, two or more osmotic delivery devices each defining a single reservoir, for example, as shown in FIG. 1, are grouped together to form a single implantable device. In this embodiment, the individual osmotic delivery device reservoirs may be attached by connecting means (e.g., biocompatible adhesives, elastomeric retaining rings, weld-joints, or tongue and groove connections).

The ends of the devices comprising the semi-permeable membrane are typically adjacent as the diffusion moderator ends of the device are also typically adjacent. Usually the ends of the devices are aligned; but the ends of the devices may also be staggered.

Devices of this type have the advantage of requiring only a single implantation while being useful for the delivery of, for example, multiple beneficial agent formulations in the same vehicle, multiple beneficial agent formulations in different vehicles, as well as multiple beneficial agent formulations for delivery at different rates.

2.1.2.3 Single Device, Two Beneficial Agent Chambers

Another embodiment of the present invention provides essentially for two osmotic delivery systems within a single device. Examples of such devices include the following specific embodiments.

2.1.2.3.1 Concentric Devices

One embodiment of the present invention provides a single delivery device having a first beneficial agent reservoir within a second beneficial agent reservoir, wherein the first beneficial agent reservoir and the second beneficial agent reservoir are essentially concentric. In this embodiment, a first substantially columnar reservoir is provided within a second substantially columnar reservoir. The inner reservoir may be stabilized within the outer reservoir by, for example, an essentially donut shaped semi-permeable membrane received in one end of the outer reservoir in sealing relationship with the inner surface of the outer reservoir, which also embraces the outer surface of the inner reservoir in sealing relationship. Similarly, the diffusion moderator may stabilize the inner reservoir within the outer reservoir. Exact alignment of the components of the inner device is not required with the components of the outer device, for example, the semi-permeable membrane of the inner device may be longer or shorter than the semi-permeable membrane of the outer device, though of smaller diameter.

In this embodiment, each of the inner and outer devices has its own diffusion moderator that defines a flow path from its respective beneficial agent chamber to an exit orifice. The flow path for the outer device may, for example, be formed by a channel created between the outer surface of the inner reservoir and the inner surface of the diffusion moderator.

Further, the exterior surface of the inner reservoir may be treated with a substance, such as a polymer or elastomer, that permits smooth operation of the essentially donut-shaped piston over the outer surface of the second reservoir.

Figure 5A:
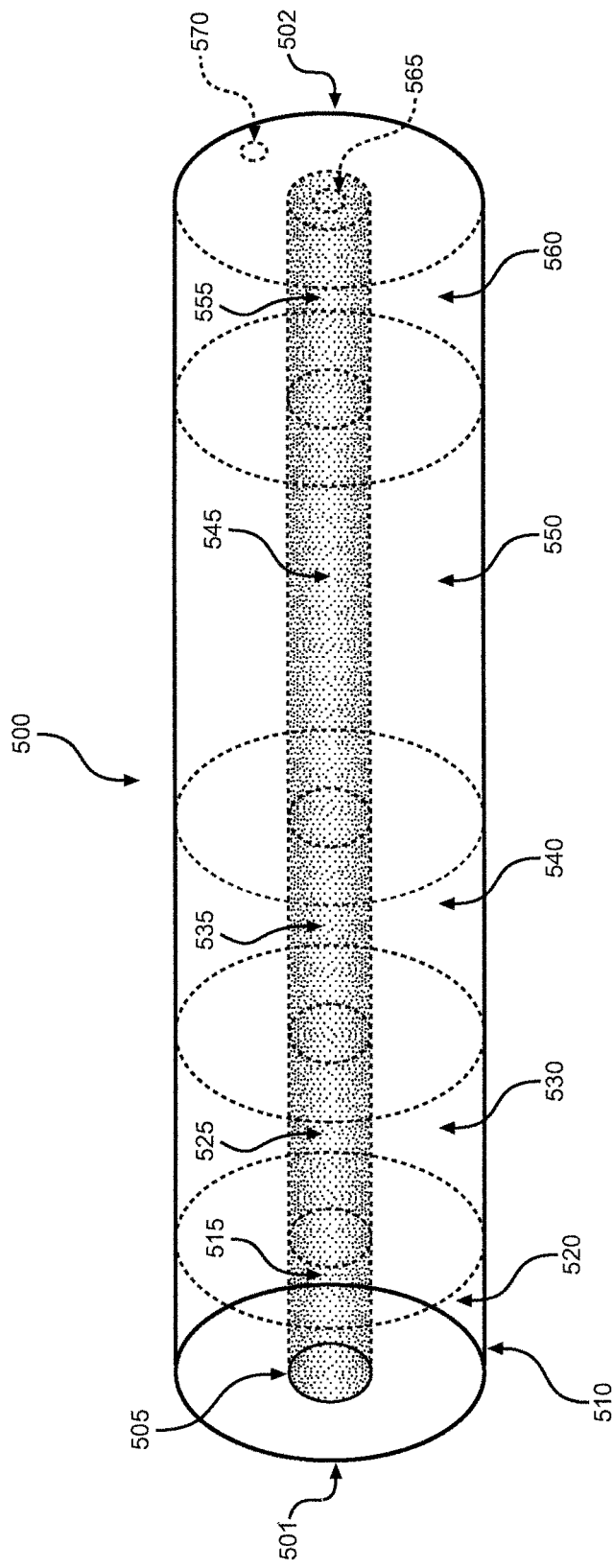
FIG. 5A illustrates a side view of an osmotic delivery device having a first beneficial agent reservoir within a second beneficial agent reservoir, wherein the first beneficial agent reservoir and the second beneficial agent reservoir are essentially concentric.

An example of this embodiment of an osmotic delivery device of the present invention 500 is illustrated in FIG. 5A to FIG. 5E. In FIG. 5A the inner reservoir is shown in grey. The outer surface 505 of the inner reservoir provides the contact surface for the osmotic components of the outer reservoir. The outer surface of the outer reservoir 510 is the exterior surface of the device. A semi-permeable membrane 515 is in sealing relationship with one end of the inner reservoir and a semi-permeable membrane 520 is in sealing relationship with one end of the outer reservoir. The semi-permeable membrane 520 may have a donut-like shape to provide a sealing relationship with the outer surface 505 of the inner reservoir as well as the inner surface of the outer reservoir. Further, a single component may comprise both semi-permeable membranes, for example, as a plug having a donut-like outer portion, which provides a sealing relationship between the inner surface of the outer reservoir and the outer surface of the inner reservoir, and a nipple-like inner portion that provides a sealing relationship with the inner surface of the inner reservoir.

Adjacent the semi-permeable membrane in both reservoirs are osmotic agent chambers 525, 530 formed between the semi-permeable membranes 515, 520 and the piston assemblies 535, 540. Adjacent the pistons in both reservoirs are beneficial agent chambers 545, 550 formed between the pistons 535, 540 and the diffusion moderators 555, 560.

Figure 5B:
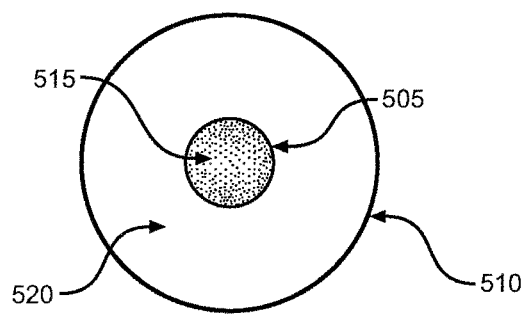
FIG. 5B illustrates a cross-section of the semi-permeable membrane end (FIG. 5A, 501) of the device.

FIG. 5B illustrates a cross-section of the semi-permeable membrane end of the device (FIG. 5A, 501). FIG. 5B shows the semi-permeable membrane for the inner reservoir 515, which is in sealing relationship with the inner surface of the inner reservoir, and the semi-permeable membrane for the outer reservoir 520, which is in sealing relationship with the outer surface of the inner reservoir 505 and the inner surface of the outer reservoir 510. As mentioned above, a single component may comprise the two semi-permeable membranes. Alternately, each semi-permeable membrane may be an individual component. Accordingly, the semi-permeable membranes may be made of the same material or of different materials.

Figure 5C:
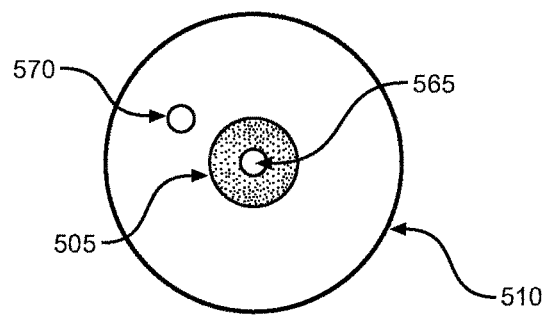
FIG. 5C illustrates an end view of the diffusion moderator end (FIG. 5A, 502) of the device.

FIG. 5C illustrates an end view of the diffusion moderator end of the device (FIG. 5A, 502). Each beneficial agent chamber is in operative contact with a flow path that leads to an exit orifice. The exit orifice 565 for the beneficial agent chamber of the inner reservoir is typically adjacent the exit orifice 570 for the beneficial agent chamber of the outer reservoir. However, the exit orifice for the outer reservoir may also be, for example, located on the side of the device.

Figure 5D:
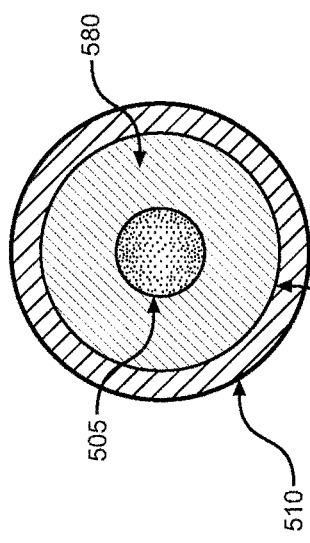
FIG. 5D illustrates a cross-sectional view of a diffusion moderator of the device presenting an example of a donut-like relationship for the diffusion moderator of the outer reservoir relative to the inner reservoir. An illustration of a flow path is shown in FIG. 5E.
Figure 5E:
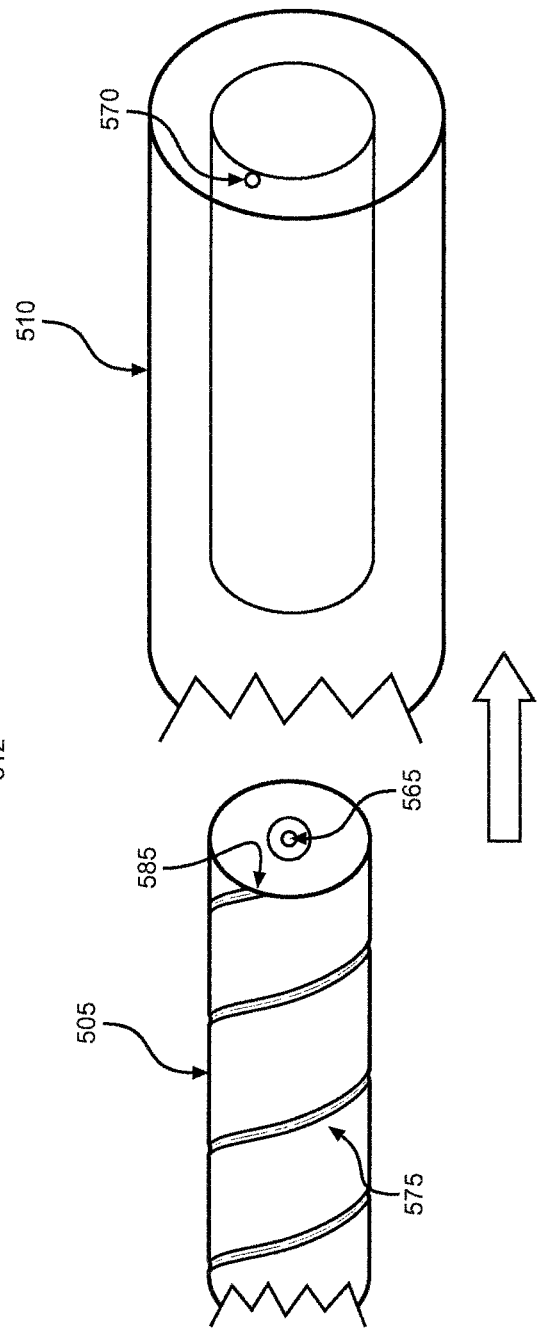

FIG. 5D illustrates an example of a donut-like diffusion moderator of the outer reservoir. The diffusion moderator of the outer reservoir 580 has a donut-like shape that contacts in mating relationship the outer surface 505 of the inner reservoir and contacts in mating relationship the inner surface of the outer reservoir 512. In some embodiments the flow path between the beneficial agent chamber of the outer reservoir is formed in part by etching, grooving or engraving the flow path on the inner surface of the outer diffusion moderator 580 with the other part of the flow path formed by the outer surface 505 of the inner reservoir. In other embodiments the flow path is formed in part by etching, grooving or engraving the flow path on the outer surface 505 of the inner reservoir with the other part of the flow path formed by the inner surface of the outer diffusion moderator 580. An illustration of such a flow path 575 is shown in FIG. 5E. The two components shown in FIG. 5E are normally in mating relationship but are shown separately to illustrate the flow path. The etched, grooved, or engraved flow path creates a functional channel when it is in mating relationship with the interior surface of the exterior reservoir. The end of the flow channel 585 is aligned with an exit orifice 570. In alternative embodiments, the diffusion moderator can, for example, (i) be press-fit (or friction fit) through an opening and contacting a smooth interior surface of the reservoir, or (ii) comprise two pieces with an outer shell constructed and arranged for positioning in an opening, an inner core inserted in the outer shell, and a fluid channel having a spiral shape defined between the outer shell and the inner core (e.g., U.S. Patent Publication No. 2007-0281024).

In some embodiments, additional means are provided to hold the first beneficial agent reservoir within and in fixed-position relative to the second beneficial agent reservoir, for example, a cap-like structure at the semipermeable membrane end comprising an opening to allow appropriate fluid imbibition, a cap-like structure at the diffusion moderator end comprising one or more openings to allow appropriate release of the beneficial agent formulation, retaining means as part of one or both of the semi-permeable membranes and/or diffusion modulators, structures at or near one or both ends of the device (e.g., single or multiple supports connecting the inner surface of the outer reservoir to the outer surface of the inner reservoir), structures at or near the semipermeable membrane surface abutting the chamber containing the osmotic agent formulation (e.g., single or multiple supports connecting the inner surface of the outer reservoir to the outer surface of the inner reservoir), and/or structures at or near the diffusion moderator surface abutting the chamber containing the beneficial agent formulation (e.g., single or multiple supports connecting the inner surface of the outer reservoir to the outer surface of the inner reservoir).

Devices of this type have the advantage of requiring only a single implantation while being useful for the delivery of, for example, multiple beneficial agent formulations in the same vehicle, multiple beneficial agent formulations in different vehicles, as well as multiple beneficial agent formulations for delivery at different rates.

2.1.2.3.2 Opposite End Orifices

In another embodiment of the present invention a device for dual osmotic delivery is provided that has centrally located semi-permeable membranes for fluid imbibition and distally located diffusion moderators for release of the beneficial agent formulations. Typically the device comprises a single, essentially columnar reservoir wherein an opening, or series of openings (e.g., a staggered ring of small holes drilled around the circumference of the reservoir), is formed near the center of the reservoir. This opening, or series of openings, allows fluid to flow into an interior chamber of the reservoir.

This interior, fluid imbibition chamber of the reservoir is flanked on each side by a semi-permeable membrane held in sealing relationship with the interior surface of the reservoir. Adjacent each semi-permeable membrane is an osmotic agent chamber formed between the semi-permeable membranes and piston assemblies located within the reservoir. Adjacent each piston assembly is a beneficial agent chamber that is formed between the piston assemblies and the diffusion moderators at each end of the device. Each diffusion moderator provides a flow path and an exit orifice for the beneficial agent reservoir with which it is in fluid communication.

Figure 6:
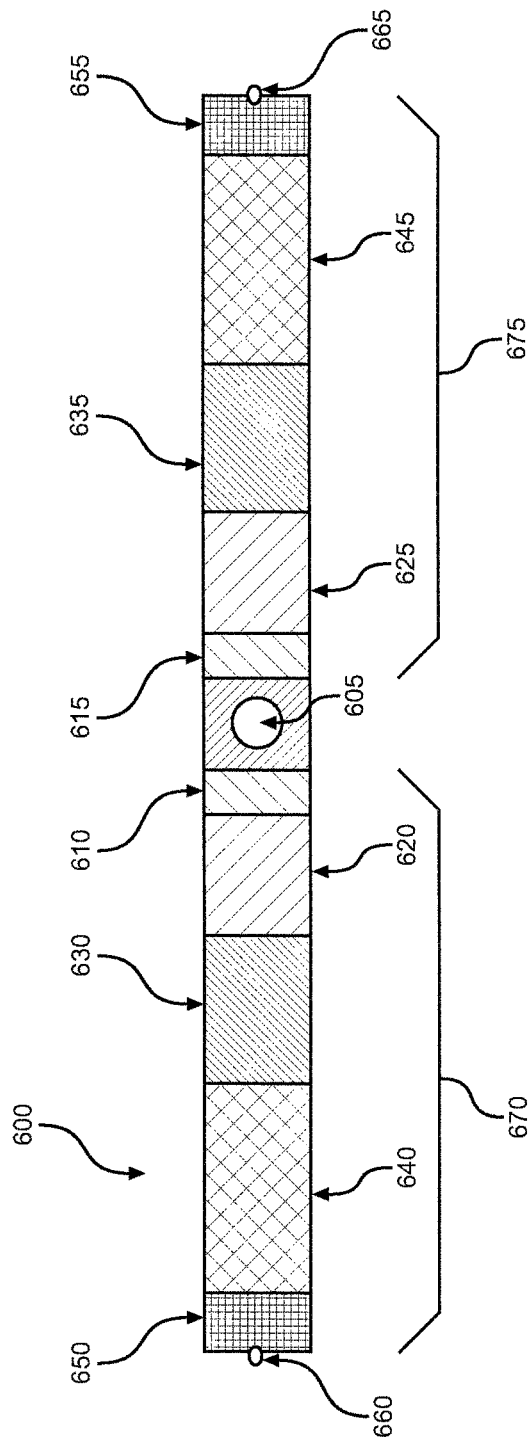
FIG. 6 illustrates a device for dual osmotic delivery that has centrally located semi-permeable membranes for fluid imbibition and distally located diffusion moderators for release of the beneficial agent formulations.

FIG. 6 presents a schematic illustration of an example of this type of device 600. In FIG. 6, an opening for fluid imbibition 605 is centrally located in the reservoir, thus forming within the lumen of the reservoir a chamber into which fluids from outside of the device may move into the interior space of the device. Adjacent to the chamber for fluid imbibition are two semi-permeable membranes 610, 615 in sealing relationship with the interior surface of the reservoir that create the ends of the fluid imbibition chamber. Adjacent each semi-permeable membrane an osmotic agent chamber 620, 625 is formed in the lumen of the reservoir between the semi-permeable membrane and the piston assemblies 630, 635. Adjacent each piston assembly a beneficial agent chamber 640, 645 is formed in the lumen of the reservoir between the piston assembly and the diffusion moderators 650, 655. Each diffusion moderator creates a flow path between its adjacent beneficial agent chamber and an orifice 660, 665 through which each beneficial agent formulation exits the device.

Another example of how this device can be configured with semi-permeable membranes is that the device can comprise two reservoir components (FIG. 6, 670, 675) that are held together in sealing, mating relationship with a centralized semi-permeable membrane. This centralized semi-permeable membrane provides a path of fluid imbibition into each of the osmotic agent chambers 620, 625 and would replace the central chamber with an opening (FIG. 6, 605).

Devices of this type have the advantage of requiring only a single implantation while being useful for the delivery of, for example, multiple beneficial agent formulations in the same vehicle, multiple beneficial agent formulations in different vehicles, as well as multiple beneficial agent formulations for delivery at different rates.

2.1.2.3.3 Opposite End Semi-Permeable Membranes

In another embodiment of the present invention, a device for dual osmotic delivery is provided that has centrally located diffusion moderators for release of the beneficial agent formulations and distally located semi-permeable membranes for fluid imbibition. Typically the device comprises a single, essentially columnar reservoir. A semi-permeable membrane is provided at each end of the reservoir and is held in sealing relationship with the interior surface of the reservoir. Adjacent each semi-permeable membrane is an osmotic agent chamber formed between the semi-permeable membranes and piston assemblies located within the reservoir. Adjacent each piston assembly is a beneficial agent chamber that is formed between the piston assemblies and the diffusion moderators centrally located within the device. Each diffusion moderator provides a flow path and an exit orifice for the beneficial agent reservoir with which it is in fluid communication.

FIG. 7A presents a schematic illustration of an example of this type of device 700. At each end of the reservoir a semi-permeable membrane 705, 710 is provided in sealing relationship with the interior wall of reservoir. Adjacent each semi-permeable membrane an osmotic agent chamber 715, 720 is formed between the semi-permeable membrane 705, 710 and the piston assembly 725, 730. Adjacent each piston assembly 725, 730, a beneficial agent chamber 735, 740 is formed between the piston assembly 725, 730 and the diffusion moderator 750. The diffusion moderator defines a flow path and an exit orifice 751, 752 for each beneficial agent chamber.

The diffusion moderator may, for example, be a single component as illustrated in FIG. 7B. The flow paths may, for example, be etched, grooved, or engraved on the exterior surface of the diffusion moderator such that a flow path 755 (terminating at 753), 760 (terminating at 754) from each beneficial agent chamber 735, 740 to an associated exit orifice 751, 752 is created, for example, the termination point 753 is aligned with exit orifice 751 and termination point 754 is aligned with exit orifice 752, thus providing a flow path for liquid from within each beneficial agent chamber to the exterior of the device. The exit orifices may be formed, for example, by boring holes in the reservoir.

In alternative embodiments, the diffusion moderator can, for example, (i) be press-fit (or friction fit) and contact a smooth interior surface of the reservoir, or (ii) comprise two pieces with an outer shell constructed and arranged for positioning in an opening, an inner core inserted in the outer shell, and fluid channels defined between the outer shell and the inner core (e.g., U.S. Patent Publication No. 2007-0281024).

Alternately, a diffusion moderator may be located at the end of each beneficial agent chamber and a diffusion chamber created between the two diffusion moderators. The flow paths defined by the two diffusion moderators may provide an avenue of fluid communication between each beneficial agent chamber and the diffusion chamber. In this case, one or more exit orifice from the device can be provided for the beneficial agent formulations to exit from the diffusion chamber of the device.

Another example of how this device can be configured with diffusion moderators is that the device can comprise two reservoir components (FIG. 7A, 775, 780) that are held together in mating relationship with a centralized diffusion moderator. This centralized diffusion moderator provides a flow path that connects each beneficial agent chamber to an exit orifice, that is, each beneficial agent chamber has a flow path to an associated orifice similar to the diffusion moderator shown in FIG. 7B.

Devices of this type have the advantage of requiring only a single implantation while being useful for the delivery of, for example, multiple beneficial agent formulations in the same vehicle, multiple beneficial agent formulations in different vehicles, as well as multiple beneficial agent formulations for delivery at different rates.

2.1.3 Examples of Component Materials

The following materials are examples of materials that can be used to make the components of the above-described devices.

The pistons of the present invention are typically columnar in shape and may be solid or hollow (e.g., donut-like) depending on the type of device. The columnar body is preferably made of a polymeric material that is substantially impermeable to and substantially resistant to leaching when exposed to any solvent, for example, an organic solvent, used in the beneficial agent formulation. Examples of polymeric materials suitable for making the body of the piston assembly include, but are not limited to, the following: polyethylene (e.g., ultra high molecular weight polyethylene (UHMWPE)); polyaryletherketones (e.g., polyetherketone and polyetheretherketone (PEEK)); and ultra-high-molecular-weight polyethylene. Other examples of useful polymers include, but are not limited to, the following: perfluoronated elastomers and polymers (e.g., elastomeric materials having broad chemical resistance, combining the resilience and sealing force of an elastomer with chemical resistance approaching that of polytetrafluoroethylene (PTFE) as available, for example, CHEMRAZ® (Greene, Tweed of Delaware, Inc., Wilmington, Del.) materials); polyimides; and polysulfones. In a preferred embodiment the polymeric material has some natural lubricity relative to the material comprising the inner wall of the lumen. The polymeric material may be one that adheres to the wall of the reservoir upon wetting. Piston assemblies may be a single component or a collection of components. For example, a substantially rigid piston may be formed wherein the surface of the piston is scored to provide a groove for the placement of an o-ring to provide an additional sealing component for contact with the interior surface of the reservoir.

In addition to use of a solid core of the polymeric materials to make the piston assembly, a thick impermeable coating of one or more solvent resistant polymer on a dissimilar core substrate may be used. Elastomers, for example, perfluoroelastomer, typically have broad chemical resistance. As an alternative to the elastomers coating an entire piston core, a thin, perfluoroelastomer O-ring, gasket, or coating may be installed on to or applied to on a rigid core material (e.g., thermoplastic, ceramic, metal) to create an acceptable piston seal. In addition a metal spring (e.g., a canted coil spring) may be used to apply a force to a portion of the surface of the piston against the inner wall of the reservoir to create an acceptable seal.

Furthermore, although an exemplary shape of the piston is described as a cylinder, the shape of the piston assembly may vary from a cylindrical shape (e.g., the piston may have an hour glass shape that contacts with the inner surface of the lumen near the distal ends). Shape of the piston assembly is typically such that it contacts the inner surface of the lumen to (i) provide separation between the beneficial agent chamber and the osmotic agent chamber of the lumen, and (ii) prevent flow-through there between. In preferred embodiments, the piston assembly substantially prevents fluid exchange between the beneficial agent chamber and the osmotic agent chamber of the lumen.

Semi-permeable materials suitable for the semi-permeable membrane are those that can conform to the shape of the lumen of the reservoir upon wetting. Preferably, these materials can also adhere to the wall of the reservoir upon wetting, thereby providing or maintaining a seal between the wall and the semi-permeable membrane. Typically, these semi-permeable materials are polymeric materials, which can be selected based on the permeability of the membrane and system configuration requirements. Examples of suitable semi-permeable materials include, but are not limited to, plasticized cellulosic materials; enhanced polymethyl methacrylates (PMMAs) such as hydroxyethylmethacrylate (HEMA); and elastomeric materials such as polyurethanes, polyetherurethane, polyetherurethane copolymers and polyamides, polyether-polyamind copolymers, thermoplastic copolyesters; and the like. Semi-permeable membranes are typically formed as plugs that provide a sealing relationship with the interior surface of each reservoir in which they come in contact.

Generally the membrane permeability ranges of the polymeric material is selected in order to provide the appropriate influx of aqueous solution into the lumen of the osmotic delivery device such that the osmotic agent expands at a rate determined to provide delivery of a beneficial agent at a desired rate for a selected period of time. In one embodiment of the present invention, the semi-permeable membrane is an aliphatic, polyether-based polyurethane. The thermoplastic polyurethane may be injection molded to form a membrane with barbed, concentric ribs and an enlarged portion that acts as a stop member. Semipermeable membranes for use in the present invention are typically plug-shaped and may, for example, have a treaded surface or annular ribs to sealingly engage grooves on the interior surface of a reservoir, have a treaded surface or annular ribs to sealingly engage a smooth interior surface of a reservoir, be adapted to press-fit (or friction fit) through an opening and contact a smooth interior surface of the reservoir, and so on. Examples of semipermeable membranes useful in the practice of the present invention have been described (e.g., U.S. Pat. Nos. 6,113,938, 6,270, 787, 6,287,295, 6,375,978, 7,163,688; U.S. Published Patent Application Nos. 2005-0010196, 2005-0101943).

The osmotic agent (or water-swellable agent) formulation (e.g., in the osmotic agent chamber) is preferably a tissue tolerable formulation whose high osmotic pressure and high solubility propels the beneficial agent over a long period of time while remaining in saturated solution in the water admitted by the semi-permeable membrane. The osmotic agent is preferably selected for tolerability by subcutaneous tissue, at least at pumping rates and hypothetically resulting concentrations to allow inadvertent dispensing from implanted devices left in the patient for a longer than the labeled period. In preferred embodiments, the osmotic agent does not diffuse or permeate through the piston assembly to any appreciable amount (e.g., less than about 10%, more preferably less than about 8%, more preferably less than about 6%) under normal operating conditions.

The osmotic agent formulation may be, for example, in the form of tablets. One or more such tablets may be used. Alternatively, the osmotic agent formulation may have other shape, texture, density, and/or consistency. For example, the osmotic agent formulation may be a slurry, a tablet, a molded or extruded material, a powder or granular form, or other form known in the art. The osmotic agent formulation may include one or more osmotic polymers. An osmotic polymer is a hydrophilic polymer that can imbibe aqueous fluids (such as biological fluids and water) and upon imbibing aqueous fluids expands to an equilibrium state and retains a significant portion of the imbibed fluid. An osmotic polymer can expand to a very high degree, for example, about 2 to about 50 times its initial volume. An osmotic polymer may or may not be cross-linked. Preferred osmotic polymers are hydrophilic polymers that are lightly cross-linked, such cross-links being formed by covalent or ionic bonds or residue crystalline regions after swelling. Osmotic polymers may be, for example, of plant, animal or synthetic origin.

Examples of osmotic polymers suitable for use in the osmotic agent formulation include, but are not limited to, poly (hydroxy-alkyl methacrylate) having a molecular weight of from 30,000 to 5,000,000; polyvinylpyrrolidone (PVP) having a molecular weight of from 10,000 to 360,000; anionic and cationic hydrogels; polyelectrolytes complexes; polyvinyl alcohol having a low acetate residual, cross-linked with glyoxal, formaldehyde, or glutaraldehyde and having a degree of polymerization of from 200 to 30,000; a mixture of methyl cellulose, cross-linked agar and carboxymethyl cellulose; a mixture of hydroxypropyl methylcellulose and sodium carboxymethylcellulose; a mixture of hydroxypropyl ethylcellulose and sodium carboxymethyl cellulose; sodium carboxymethylcellulose; potassium carboxymethylcellulose; a water insoluble, water swellable copolymer formed from a dispersion of finely divided copolymer of maleic anhydride with styrene, ethylene, propylene, butylene or isobutylene cross-linked with from 0.001 to about 0.5 moles of saturated cross-linking agent per mole of maleic anhydride per copolymer; water swellable polymers of N-vinyl lactams; polyoxyethylene-polyoxypropylene gel; polyoxybutylene-polyethylene block copolymer gel; carob gum; polyacrylic gel; polyester gel; polyuria gel; polyether gel; polyamide gel; polypeptide gels; polyamino acid gels; polycellulosic gel; polygum gel; and initially dry hydrogels that imbibe and absorb water that penetrates the glassy hydrogel and lowers its glass temperature.

Other examples of osmotic polymers include, but are not limited to, the following: polymers that form hydrogels such as CARBOPOL® (Noveon, Inc., Cleveland, Ohio), acidic carboxypolymer, a polymer of acrylic and cross-linked with a polyallyl sucrose, also known as carboxypolymethylene and carboxyvinyl polymer having a molecular weight of 250,000 to 4,000,000; cynamer polyacrylamides; cross-linked water swellable indene-maleic anhydride polymers; GOODRITE® (Noveon, Inc., Cleveland, Ohio) polyacrylic acid having a molecular weight of 80,000 to 200,000; POLYOX® (Union Carbide Chemicals & Plastics Technology Corporation, Danbury, Conn.) polyethylene oxide polymer having a molecular weight of 100,000 to 5,000,000 and higher; starch graft copolymers; acrylate polymer polysaccharides composed of condensed glucose units such as diester cross-linked polygluran; and the like.

The osmotic agent formulation may include an osmotic effective solute either in addition to or in lieu of the osmotic polymer described above. Osmotic effective solutes include inorganic and organic compounds that can exhibit an osmotic pressure gradient across the semi-permeable membrane when the osmotic delivery system is placed in a fluid environment. An osmotic effective solute in the osmotic agent formulation imbibes fluid into the osmotic agent chamber through the semi-permeable membrane, thereby making available fluid pressure to displace the piston assembly and push the beneficial agent formulation through the delivery (or exit) orifice via the diffusion moderator. Osmotic effective solutes or osmagents (i.e., the non-volatile species that are soluble in water and create the osmotic gradient driving the osmotic inflow of water) useful in the osmotic agent formulation include, but are not limited to, magnesium sulfate, magnesium chloride, sodium chloride, potassium sulfate, sodium sulfate, lithium sulfate, sodium phosphate, potassium phosphate, d-mannitol, urea, inositol, magnesium succinate, tartaric acid, inositol, carbohydrates, and various monosaccharides, oligosaccharides and polysaccharides such as sucrose, glucose, lactose, fructose, raffinose and dextran, as well as mixtures of any of these various species.

Osmotic agents such as sodium chloride (NaCl) with appropriate tabletting agents (lubricants and binders; e.g., cellulosic and povidone binders) and viscosity modifying agents, such as sodium carboxymethylcellulose or sodium polyacrylate are examples of preferred osmotic agents. Other osmotic agents useful as the water-swellable agent include osmopolymers and osmagents and are described, for example, in U.S. Pat. No. 5,413,572. A liquid or gel additive or filler may be added to the chamber containing the osmotic agent formulation to exclude air spaces. Exclusion of air from the devices generally means that delivery rates will be less affected by nominal external pressure changes.

Materials that may be used for the reservoir are sufficiently rigid to withstand expansion of the osmotic agent formulation without changing its size or shape. Where the osmotic delivery system is implantable, the materials are typically selected to ensure that the reservoir will not leak, crack, break, or distort under stresses to which it may be subjected during implantation or under stresses due to the pressures generated during operation. The reservoir may be formed of non-reactive (or inert), biocompatible, natural or synthetic materials that are known in the art. Preferably, the material of the reservoir is non-bioerodible. Generally, preferred materials for the reservoir are those acceptable for human implantation. Preferably, the material of the reservoir is impermeable, particularly when stability of the formulation in the reservoir is sensitive to fluids in the fluid environment of use (e.g., after implantation in a subject).

Examples of materials suitable for the reservoir include non-reactive, biocompatible polymers and metals or alloys. Examples of non-reactive, biocompatible polymers for the reservoir include, but are not limited to, acrylonitrile polymers such as acrylonitrile-butadiene-styrene terpolymer; halogenated polymers such as polytetrafluoroethylene, polychlorotrifluoroethylene, copolymer tetrafluoroethylene and hexafluoropropylene; polyimide; polysulfone; polycarbonate; polyethylene; polypropylene; polyvinylchloride-acrylic copolymer; polycarbonate-acrylonitrile-butadiene-styrene; and polystyrene. Examples of metallic, biocompatible materials for the reservoir include, but are not limited to, stainless steel, titanium, platinum, tantalum, gold, and their alloys, as well as gold-plated ferrous alloys, platinum-plated ferrous alloys, cobalt-chromium alloys and titanium nitride coated stainless steel. For size-critical applications, high payload capabilities, long duration applications, and applications where the formulation is sensitive to body chemistry at the implantation site, the reservoir is preferably made of titanium or a titanium alloy having greater than about 60%, more preferably greater than about 85% titanium.

The total size of the reservoir is selected based on a variety of parameters, for example, (i) the volume occupied by a diffusion moderator, (ii) the volume occupied by an beneficial agent formulation, (iii) the volume occupied by a piston assembly, (iv) the volume occupied by an osmotic agent formulation, (v) the volume occupied by a semi-permeable membrane, and (vi) the number of beneficial agent chambers.

The diffusion moderator is typically a plug-like member defining a liquid flow path for exit of the beneficial agent formulation from the osmotic delivery system (e.g., U.S. Pat. Nos. 5,728,396, 5,997,527, 6,217,906, 6,287,295, 6,395,292, 6,524,305, 6,635,268, 6,840,931, and 6,923,800; U.S. Patent Application Publication No. 2005-0175701, 2007-0281024).

The present invention is not limited to any particular diffusion moderator as long as the diffusion moderator is able to deliver the beneficial agent formulation in a desired manner. Preferably, the diffusion moderator allows delivery of the beneficial agent formulation while controlling back-diffusion of external fluid into the lumen of the reservoir. The distal end may be open and the diffusion moderator may be provided in the form of a plug that is inserted in the open end. Alternately, the diffusion moderator may be integrated with a distal end of the reservoir.

The delivery orifice flow channel provided by the diffusion moderator may be, for example, spiral in shape or straight. Further, the orifice flow channel may be of a variety of shapes including, but not limited to, circular, triangular, square, D-shaped, oval, or elongated (e.g., slit-like). The diffusion moderator is preferably made of a non-reactive (or inert), biocompatible material. Exemplary materials include, but are not limited to, metals such as titanium, stainless steel, platinum and their alloys, and cobalt-chromium alloys. Other compatible materials include polymers such as polyethylene, polypropylene, polycarbonate, polymethylmethacrylate, and polyaryletherketones, e.g., polyetheretherketone (PEEK). Typically, the flow channel has a nominal "diameter" (i.e., measured across the widest opening) of between about 0.05 mm to about 0.75 mm, preferably between about 0.15 mm to about 0.50 mm. In one embodiment, the orifice flow channel is a D-shaped channel having a nominal "diameter" of about 250 µm (about 0.25 mm).

The diffusion moderator may be assembled to the reservoir by using a number of methods, for example, a thread and screw method wherein the diffusion moderator or the interior surface of the lumen or both comprise ribs, for example, complementary continuous helical threads/grooves. Single, double, triple, or quadruple threads/grooves may be used.

Alternatively, the diffusion moderator may be assembled to the reservoir by a press-fit (i.e., interference fit) where the outside of the diffusion moderator is slightly larger than the inside diameter of the reservoir. Typically, this assembly method is faster and easier to automate than other assembly methods that may be used in the practice of the present invention such as thread and screw assemblies.

An osmotic delivery system diffusion moderator assembly may also include, for example, a body defining an open pathway (e.g., a hole or flow channel) through the body of the diffusion moderator that communicates between two opposing ends of the body (e.g., where the orifice defines the exit site of the beneficial agent). The open pathway may be, for example, straight, spiral, or curved. The diffusion moderator may further comprise a stopper that serves to close the orifice to the external environment until the osmotic delivery system is ready for use (e.g., U.S. Pat. No. 6,524,305). Prior to use, such a stopper is removed.

In one embodiment, the diffusion moderator comprises two parts (e.g., two polyetheretherketone machined parts as described in U.S. Patent Publication No. 2007-0281024), an inner core and an outer sleeve, whereby a continuous spiral delivery channel is formed between the two parts when they are assembled. The two-piece moderator is assembled by press-fitting into the reservoir (wherein neither the reservoir nor the moderator comprises ribs). In other embodiments, ribbed components may be used. Such two-piece diffusion moderators can be adapted for use in all embodiments of osmotic delivery devices described herein.

Delivery rates of beneficial agent formulations from the osmotic delivery devices of the present invention may be varied by, for example, using different diffusion moderator flow path sizes (e.g., length or width), different semi-permeable membranes associated with separate osmotic agent chambers, different osmotic agents within different osmotic agent chambers wherein, for example, the osmotic agents have different expansion properties.

The present invention also includes methods of manufacturing the osmotic delivery systems of the present invention. Typically a method of manufacturing comprises providing the device components and positioning the components in appropriate functional relationship with each other, as described herein, to make the osmotic delivery device. Such methods also typically comprise filling the appropriate chambers with one or more osmotic agent formulation and filling the appropriate chambers with one or more beneficial agent formulation.

Furthermore, the osmotic delivery systems of the present invention may be individually packaged or packaged in groups. Such packaging may be, for example, foil pouches or vials. The packaging may include a desiccant or the osmotic delivery systems may be packaged under nitrogen or vacuum.

Examples of beneficial agents and beneficial agent formulations for use in the practice of the present invention are discussed further herein below and these beneficial agents may be used singly in formulations or in the described combined formulations. Accordingly, an osmotic delivery device having two beneficial agent chambers can be used, for example, to administer two beneficial agents, wherein each beneficial agent is prepared in a separate formulation, or to deliver more than two beneficial agents, wherein two or more beneficial agents are formulated together for delivery from at least one of the beneficial agent chambers.

2.1.4 Advantages of the Devices of the Present Invention

The devices of the present invention that provide multiple beneficial agent chambers provide many advantages for the administration of beneficial agent formulations including, but not limited to, the following. First, within a single device a beneficial agent may be delivered for a short period of time (e.g., weeks or months), for example, to begin therapy, and a second beneficial agent may be delivered for a longer period of time (e.g., weeks, months, or even a year or more). Alternatively, the same beneficial agent may be provided at a different dosage in one beneficial agent chamber relative to another beneficial agent chamber to provide step-down or step-up administration of the beneficial agent.

An example of step-down administration is if beneficial agent formulation A is delivered at amount X from beneficial agent chamber 1, and the same beneficial agent formulation A is delivered at amount X from beneficial agent chamber 2 but a smaller volume of the beneficial agent formulation is provided in chamber 1 so that when the beneficial agent formulation from chamber 1 is depleted the amount of beneficial agent being delivered goes from 2X to X. In this example, delivery of the beneficial agent from both chambers begins concurrently.

An example of step-up administration is if beneficial agent formulation A is delivered at amount X from a first beneficial agent chamber A, and the same beneficial agent is delivered in formulation B at amount 2X from a second beneficial agent chamber B but beneficial agent chamber A has a smaller volume of the beneficial agent formulation and is associated with a semi-permeable membrane that is selected to imbibe water at a faster rate to deliver the volume from beneficial agent chamber A corresponding to the desired low dose period. The volume of beneficial agent chamber B is the same or larger and is associated with a semi-permeable membrane that imbibes water at a slower rate providing a longer duration of dosing. Beneficial agent chamber B is partially filled with a viscous formulation of beneficial agent comprising a concentration of the beneficial agent to deliver 2X. The remainder of the beneficial agent chamber B is filled with a layer of vehicle not containing the beneficial agent, the volume of this layer of vehicle and rate of water imbibed by the semi-permeable membrane are selected to correspond with the duration of dosing for beneficial agent chamber A. As beneficial agent is delivered from beneficial agent chamber A, only vehicle is being delivered from beneficial agent chamber B and when beneficial agent chamber A is depleted the beneficial agent is delivered from beneficial agent chamber B at a rate of 2X.

A second advantage of the devices of the present invention can be seen from the previous description wherein delivery of a first beneficial agent from the first beneficial agent chamber is of different duration than delivery of a second beneficial agent from the second beneficial agent chamber.

A third advantage of the devices of the present invention is that delivery of a first beneficial agent from the first beneficial agent chamber is at a different rate than delivery of a second beneficial agent from the second beneficial agent chamber.

A fourth advantage of the devices of the present invention is that they can provide, from a single device, delivery of multiple beneficial agents from the same device when the beneficial agents cannot be formulated together, for example, because of drug incompatibility or different vehicle requirements (e.g., solubility differences of the beneficial agents in solvents/polymers). Multiple beneficial agent chambers offer formulation flexibility because, for example, different solvents, vehicles, particles, and strength combinations can be used in separate beneficial agent chambers.

A fifth advantage of the devices of the present invention is to provide co-administration of two or more beneficial agents from a single device. Examples of co-administration of specific beneficial agents are described herein below.

Such implantable osmotic delivery devices can be designed to provide therapeutic doses of the drug over periods of weeks, months, or even a year or more. Implantable osmotic delivery systems, once inserted in a subject, administer therapeutic doses without relying on or requiring any action of the subject. Accordingly, compliance to a required dosing regimen is generally ensured.

2.2 Beneficial Agent Formulations

The beneficial agent formulation, which occupies a beneficial agent chamber of an osmotic delivery device, may comprise one or more beneficial agents. The beneficial agent may be any physiologically or pharmacologically active substance, particularly those known to be delivered to the body of a human or an animal such as medicaments, vitamins, nutrients, or the like. Beneficial agents that may be delivered by the osmotic delivery system of the present invention include, but are not limited to, drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system or the central nervous system. Further, beneficial agents that may be delivered by the osmotic delivery system of the present invention include, but are not limited to, beneficial agents used for the treatment of infectious diseases, chronic pain, diabetes, auto-immune disorders, endocrine disorders, metabolic disorders, oncological diseases, and rheumatologic disorders, central nervous system (CNS) related disorders, and psychiatric disorders.

2.2.1 Examples of Beneficial Agents

Suitable beneficial agents include, but are not limited to, the following: peptides, proteins, polypeptides (e.g., enzymes, hormones, cytokines), polynucleotides, nucleoproteins, polysaccharides, glycoproteins, lipoproteins, steroids, analgesics, local anesthetics, antibiotic agents, anti-inflammatory corticosteroids, ocular drugs, other small molecules for pharmaceutical use, or synthetic analogs of these species, as well as mixtures thereof. Preferred beneficial agents include macromolecules (e.g., peptides, proteins and polypeptides) or beneficial agents that are highly potent.

The osmotic devices of the invention may be used to deliver a wide variety of beneficial agents. These agents include, but are not limited to, pharmacologically beneficial peptides proteins, polypeptides, genes, gene products, other gene therapy agents, or other small molecules. The polypeptides may include but are not limited to the following: growth hormone; somatostatin; somatropin, somatotropin, somatotropin analogues, somatomedin-C, somatotropin plus an amino acid, somatotropin plus a protein; follicle stimulating hormone; luteinizing hormone, luteinizing hormone-releasing hormone (LHRH), LHRH analogues/agonists such as leuprolide, nafarelin and goserelin, LHRH antagonists; growth hormone releasing factor; calcitonin; colchicine; gonadotropins such as chorionic gonadotropin; antiandrogens such as flutamide, nilutamide and cyproterone; aromatase inhibitors such as exemastane, letrozole and anastrazole; selective estrogen receptive modulators such as raloxifene, lasoxifene; oxytocin, octreotide; vasopressin; adrenocorticotrophic hormone; epidermal growth factor; fibroblast growth factor; platelet-derived growth factor; transforming growth factor; nerve growth factor; prolactin; cosyntropin; lypressin polypeptides such as thyrotropin releasing hormone; thyroid stimulation hormone; secretin; leptin; amylin, amylin analogues (e.g., pramlintide acetate); pancreozymin; enkephalin; glucagon; endocrine agents secreted internally and distributed by way of the bloodstream; or the like.

Further beneficial agents that may be delivered include but are not limited to the following: alpha antitrypsin; factor VII; factor IX, thrombin and other coagulation factors; insulin; peptide hormones; adrenal cortical stimulating hormone, thyroid stimulating hormone and other pituitary hormones; erythropoietin; growth factors such as granulocyte-colony stimulating factor, granulocyte-macrophage colony stimulating factor, thrombopoietin, insulin-like growth factor 1; tissue plasminogen activator; CD4; 1-deamino-8-D-arginine vasopressin; interleukin-1 receptor antagonist; tumor necrosis factor, tumor necrosis factor receptor; tumor suppresser proteins; pancreatic enzymes; lactase; cytokines, including lymphokines, chemokines or interleukins such as interleukin-1, interleukin-2 and other members of the interleukin family (e.g., IL-1, 6, 12, 15, 17, 18, 32); cytotaxic proteins; superoxide dismutase; endocrine agents secreted internally and distributed in an animal by way of the bloodstream; recombinant antibodies, antibody fragments, humanized antibodies, single chain antibodies, monoclonal antibodies; avimers; or the like.

Further, the beneficial agents that may be administered include, but are not limited to, organic compounds including those compounds that transport across a vessel. Examples of beneficial agents that may be used in the practice of the present invention include, but are not limited to, the following: hypnotics and sedatives such as pentobarbital sodium, phenobarbital, secobarbital, thiopental, amides and ureas exemplified by diethylisovaleramide and alpha-bromo-isovaleryl urea, urethanes, or disulfanes; heterocyclic hypnotics such as dioxopiperidines, and glutarimides; antidepressants such as isocarboxazid, nialamide, phenelzine, imipramine, tranylcypromine, pargyline; tranquilizers such as chloropromazine, promazine, fluphenazine reserpine, deserpidine, meprobamate, benzodiazepines such as chlordiazepoxide; tricyclic antidepressants; anticonvulsants such as primidone, diphenylhydantoin, ethltoin, pheneturide, ethosuximide; muscle relaxants and anti-parkinson agents such as mephenesin, methocarbomal, trihexylphenidyl, biperiden, levodopa, also known as L-dopa and L-beta-3-4-dihydroxyphenylalanine; analgesics such as morphine, codeine, meperidine, nalorphine; antipyretics and anti-inflammatory agents such as aspirin, salicylamide, sodium salicylamide, naproxin, ibuprofen, acetaminophen; local anesthetics such as procaine, lidocaine, naepaine, piperocaine, tetracaine, dibucane; antispasmodics and antiulcer agents such as atropine, scopolamine, methscopolamine, oxyphenonium, papaverine, prostaglandins such as $PGE_1$, $PGE_2$, $PGF_{1alpha}$, $PGF_{2alpha}$, PGA; anti-microbials such as penicillin, tetracycline, oxytetracycline, chlorotetracycline, chloramphenicol, sulfonamides, bacitracin, chlorotetracycline, levofloxacin, erythromycin; anti-fungals such as Amphotericin B; antimalarials such as 4-aminoquinolines, 8-aminoquinolines and pyrimethamine; hormonal agents such as prednisolone, cortisone, cortisol and triamcinolone, androgenic steroids (for example, methyltestosterone, fluoxmesterone), estrogenic steroids (for example, 17-beta-estradoil and thinyl estradiol), progestational steroids (for example, 17-alpha-hydroxyprogesterone acetate, 19-nor-progesterone, norethindrone); sympathomimetic drugs such as epinephrine, amphetamine, ephedrine, norepinephrine; cardiovascular drugs such as procainamide, amyl nitrate, nitroglycerin, dipyridamole, sodium nitrate, mannitol nitrate; diuretics such as acetazolamide, chlorothiazide, flumethiazide; antiparasitic agents such as bephenium hydroxynaphthoate, dichlorophen, enitabas, dapsone; anti-neoplastic agents such as mechloroethamine, uracil mustard, 5-fluorouracil, 6-thioguanine, procarbazine, paclitaxel, docetaxel, carboplatin, gemcitabine, oxaliplatin, fludarabine, ara-C, camptothecin, bortezomib, methrotrexate, capecitabine, doxorubicin, vincristine, cyclophosphamide, etoposide; VEGF/EGF inhibitors (for example, small molecules and antibodies); hypoglycemic drugs such as insulin related compounds (for example, isophane insulin suspension, protamine zinc insulin suspension, globin zinc insulin, extended insulin zinc suspension) tolbutamide, acetohexamide, tolazamide, chlorpropamide; nutritional agents such as vitamins, essential amino acids, and essential fats; eye drugs such as pilocarpine base, pilocarpine hydrochloride, pilocarpine nitrate; antiviral drugs such as disoproxil fumarate, aciclovir, cidofovir, docosanol, famciclovir, fomivirsen, foscarnet, ganciclovir, idoxuridine, penciclovir, trifluridine, tromantadine, valaciclovir, valganciclovir, vidarabine, amantadine, arbidol, oseltamivir, peramivir, rimantadine, zanamivir, abacavir, didanosine, emtricitabine, lamivudine, stavudine, zalcitabine, zidovudine, tenofovir, efavirenz, delavirdine, nevirapine, loviride, amprenavir, atazanavir, darunavir, fosamprenavir, indinavir, lopinavir, nelfinavir, ritonavir, saquinavir, tipranavir, enfuvirtide, adefovir, fomivirsen, imiquimod, inosine, podophyllotoxin, ribavirin, viramidine, fusion inhibitors specifically targeting viral surface proteins or viral receptors (for example, gp-41 inhibitor (T-20), CCR-5 inhibitor, FUZEON® (Trimeris, Inc., Morrisville, N.C.; enfuvirtide)); anti-nausea (such as scopolamine, dimenhydrinate, metaclopramide, ondansetron); iodoxuridine, hydrocortisone, eserine, phospholine, iodide, as well as other beneficial beneficial agents.

Examples of beneficial agent formulations comprising a small molecule (e.g., Amphotericin B) are given in Examples 6A and 6B.

Numerous peptides, proteins, or polypeptides that are useful in the practice of the present invention are described herein. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the beneficial agents disclosed herein may be formulated singly or in combination (e.g., mixtures).

Further, oligonucleotides (e.g., RNA, DNA, alternative backbones) may be used as beneficial agents in the practice of the present invention. In one embodiment therapeutic RNA molecules may include, but are not limited to, small nuclear RNAs (snRNAs), and small interfering RNA strands (siRNA) for use in RNA interference (RNAi) inhibition of gene expression. RNAi inhibition typically occurs at the stage of translation or by hindering the transcription of specific genes. RNAi targets include, but are not limited to, RNA from viruses and genes with roles in regulating development and genome maintenance.

Some embodiments of the present invention comprise use of interferon for the treatment of interferon responsive diseases or disorders. An example of an interferon particle formulation is given in Example 5.

Some embodiments of the present invention comprise the use of peptide hormones for the treatment of diabetes and diabetes related conditions (e.g., insulinotropic peptides such as glucagon like protein (such as GLP-1), as well as analogues and derivatives thereof, or exendins (such as exendin-4), as well as analogs and derivatives thereof).

Numerous GLP-1 derivatives and analogues demonstrating insulinotropic action are known in the art (e.g., U.S. Pat. Nos. 5,118,666, 5,120,712, 5,512,549, 5,545,618, 5,574,008, 5,574,008, 5,614,492, 5,958,909, 6,191,102, 6,268,343, 6,329,336, 6,451,974, 6,458,924, 6,514,500, 6,593,295, 6,703,359, 6,706,689, 6,720,407, 6,821,949, 6,849,708, 6,849,714, 6,887,470, 6,887,849, 6,903,186, 7,022,674, 7,041,646, 7,084,243, 7,101,843, 7,138,486, 7,141,547, 7,144,863, and 7,199,217). Accordingly, for ease of reference herein, the family of GLP-1 derivatives and analogues having insulinotropic activity is referred to collectively as GLP-1.

The exendins are peptides that were isolated from the venom of the Gila-monster. Exendin-4 is present in the venom of Heloderma suspectum (Eng, J., et al., J. Biol. Chem., 265:20259-62 (1990); Eng., J., et al., J. Biol. Chem., 267: 7402-05 (1992); U.S. Pat. No. 5,424,286). Based on their insulinotropic activities, use of exendin-3 and exendin-4 for the treatment of diabetes mellitus and the prevention of hyperglycemia has been proposed (e.g., U.S. Pat. No. 5,424,286). Numerous exendin-4 derivatives, and analogues (including, e.g., exendin-4 agonists) demonstrating insulinotropic action are known in the art (e.g., U.S. Pat. Nos. 5,424,286, 6,268, 343, 6,329,336, 6,506,724, 6,514,500, 6,528,486, 6,593,295, 6,703,359, 6,706,689, 6,767,887, 6,821,949, 6,849,714, 6,858,576, 6,872,700, 6,887,470, 6,887,849, 6,924,264, 6,956,026, 6,989,366, 7,022,674, 7,041,646, 7,115,569, 7,138,375, 7,141,547, 7,153,825, and 7,157,555). Exenatide is a synthetic version of exendin-4 (Kolterman O. G., et al., J. Clin. Endocrinol. Metab. 88(7):3082-9 (2003)). Accordingly, for ease of reference herein, the family of exendin-4 polypeptides, exendin-4 derivatives, variants and analogues having insulinotropic activity is referred to collectively as exendin-4. Examples of exendin-4 particle formulations are given in Examples 1, 4A, and 4B.

Peptide YY (PYY) inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335(8705):1555-7 (1990)), stimulate net absorption (MacFayden, R. J., et al., Neuropeptides 7(3):219-27 (1986)), and two major in vivo variants (PYY and $PYY_{3-36}$) have been identified (e.g., Eberlein, G. A., et al., Peptides 10 (4), 797-803 (1989)). The sequence of PYY, as well as analogs and derivatives thereof, including $PYY_{3-36}$, are known in the art (e.g., U.S. Pat. Nos. 5,574,010 and 5,552,520). For ease of reference herein, the family of PYY polypeptides, PYY derivatives, variants and analogues are referred to collectively as PYY. Examples of PYY particle formulations are given in Examples 3 and 4B.

Oxyntomodulin is a naturally occurring 37 amino acid peptide hormone found in the colon that has been found to suppress appetite and facilitate weight loss (Wynne K, et al., Int J Obes (Lond) 30(12):1729-36 (2006)). The sequence of oxyntomodulin, as well as analogs and derivatives thereof, are known in the art (e.g., U.S. Patent Publication Nos. 2005-0070469 and 2006-0094652). For ease of reference herein, the family of oxyntomodulin polypeptides, oxyntomodulin derivatives, variants and analogues are referred to collectively as oxyntomodulin. Examples of oxyntomodulin particle formulations are given in Examples 2 and 4A.

GIP is an insulinotropic peptide hormone (Efendic, S., et al., Horm Metab Res. 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., PNAS 90:1992-1996 (1993)). The sequence of GIP, as well as analogs and derivatives thereof, are known in the art (e.g., Meier J. J., Diabetes Metab Res Rev. 21(2): 91-117 (2005); Efendic S., Horm Metab Res. 36(11-12): 742-6 (2004)). For ease of reference herein, the family of GIP polypeptides, GIP derivatives, variants and analogues are referred to collectively as GIP.

Amylin, as well as analogs and derivatives thereof, are known in the art (e.g., U.S. Pat. Nos. 5,686,411, 5,814,600, 5,998,367, 6,114,304, 6,410,511, 6,608,029, and 6,610,824). For ease of reference herein, the family of amylin polypeptides, amylin derivatives, variants and analogues are referred to collectively as amylin.

The cDNA sequence encoding the human leptin protein hormone is known (e.g., Masuzaki, H., et al. (Diabetes 44: 855-858, 1995)). Leptin, as well as analogs and derivatives thereof, are known in the art (e.g., U.S. Pat. Nos. 5,521,283, 5,525,705, 5,532,336, 5,552,522, 5,552,523, 5,552,524, 5,554,727, 5,559,208, 5,563,243, 5,563,244, 5,563,245, 5,567,678, 5,567,803, 5,569,743, 5,569,744, 5,574,133, 5,580,954, 5,594,101, 5,594,104, 5,605,886, 5,691,309, and 5,719,266; P.C.T. International Patent Publication Nos. WO96/22308, WO96/31526, WO96/34885, 97/46585, WO97/16550, and WO 97/20933; European Patent Publication No. EP 0 741 187). For ease of reference herein, the family of leptin polypeptides, leptin derivatives, variants and analogues are referred to collectively as leptin.

The beneficial agents can also be in various forms including, but not limited to, the following: uncharged molecules; components of molecular complexes; and pharmacologically acceptable salts such as hydrochloride, hydrobromide, sulfate, laurates, palmatates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein. Drug or other formulation within the osmotic delivery device beneficial agent chamber can have various art known forms such as solution, dispersion, paste, cream, particle, granule, tablet, emulsions, suspensions, powders and the like. In addition to the one or more beneficial agents, the beneficial agent formulation may optionally include pharmaceutically acceptable carriers and/ or additional ingredients such as antioxidants, stabilizing agents, buffers, and permeation enhancers.

The above agents are useful for the treatment of a variety of conditions including but not limited to hemophilia and other blood disorders, growth disorders, diabetes, leukemia and lymphoma, hepatitis, renal failure, bacterial infection, viral infection (e.g., infection by HIV, HCV, etc.), hereditary diseases such as cerbrosidase deficiency and adenosine deaminase deficiency, hypertension, septic shock, autoimmune diseases (e.g., Graves disease, systemic lupus erythematosus and rheumatoid arthritis), shock and wasting disorders, cystic fibrosis, lactose intolerance, Crohn's disease, inflammatory bowel disease, Alzheimer's disease, metabolic disorders (such as obesity), and cancers.

The amount of beneficial agent employed in the delivery device of the invention is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Beneficial agents and their dosage unit amounts are known to the prior art in Goodman & Gilman's The Pharmacological Basis of Therapeutics, 11th Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins. Typically, for an osmotic delivery device, the volume of a beneficial agent chamber comprising the beneficial agent formulation (e.g., chamber 108, FIG. 1) is between about 50 µl to about 1000 µl, more preferably between about 100 µl and about 500 µl, more preferably between about 150 µl and about 200 µl.

The vehicle for the beneficial agents typically comprises a non-aqueous, single-phase vehicle including one or more polymer and one or more solvent. The vehicle preferably exhibits viscous fluid characteristics. A polypeptide component may, for example, be in a particle formulation that is uniformly dispersed in the vehicle. Typically, the particle formulation includes a stabilizing component comprising one of more stabilizer component selected from the group consisting of carbohydrates, antioxidants, amino acids, buffers, and inorganic compounds.

2.2.2 Particle Formulations

For some beneficial agents, in particular polypeptides, particle formulations are used in the practice of the present invention. Particle formulations are preferably chemically and physically stable for at least about one month, more preferably at least about three months, more preferably at least about six months, and even more preferably at least about 12 months, at delivery temperature. The delivery temperature is typically normal human body temperature, for example, about 37° C., or slightly higher, for example, about 40° C. Further, particle formulations of the present invention are preferably chemically and physically stable for at least about three months, more preferably at least about six months, even more preferably at least about 12 months, at storage temperature. Examples of storage temperatures include refrigeration temperature, for example, about 5° C., or room temperature, for example, about 25° C.

A particle formulation may be considered chemically stable if less than about 25%, preferably less than about 20%, more preferably less than about 15%, more preferably less than about 10%, and more preferably less than about 5% breakdown products of the peptide particles are formed after about three months, preferably after about six months, preferably after about 12 months at delivery temperature and after about six months, after about 12 months, and preferably after about 24 months at storage temperature.

A particle formulation may be considered physically stable if less than about 10%, preferably less than about 5%, more preferably less than about 3%, more preferably less than about 1% aggregates of the peptide particles are formed after about three months, preferably after about six months, at delivery temperature and about six months, preferably about 12 months, at storage temperature. Another criterion for demonstrating that a particle formulation is considered physically stable is that the solid state of the particle can remain essentially the same or substantially similar (for example, the particle does not demonstrate a phase transition from amorphous to crystal or an inter-exchange between polymorphous states) for a selected period of time (e.g., after about three months, preferably after about six months, preferably after about 12 months at delivery temperature and after about six months, preferably after about 12 months, and more preferably after about 24 months at storage temperature).

To preserve protein stability generally a protein solution is kept in a frozen condition and lyophilized or spray dried to a solid state. Tg (glass transition temperature) may be one factor to consider in achieving stable compositions of protein. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., protein products will not have mobility when stored at room temp or even at 40° C. because the storage temperature is below the Tg. Calculations using molecular information have shown that if a glass transition temperature is above a storage temperature of 50° C. that there is zero mobility for molecules. No mobility of molecules correlates with no instability issues. Tg is also dependent on the moisture level in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. The particles are preferably substantially uniform in shape and size.

A typical spray dry process may include, for example, loading a spray solution containing a peptide, for example, omega interferon, and stabilizing excipients into a sample chamber. The sample chamber is typically maintained at a desired temperature, for example, refrigeration to room temperature. Refrigeration generally promotes stability of the protein. A feed pump sprays the spray solution into a nozzle atomizer. At the same time, atomized gas (typically, air, nitrogen, or inert gas) is directed at the outlet of the nozzle atomizer to form a mist of droplets from the spray solution. The mist of droplets is immediately brought into contact with a drying gas in a drying chamber. The drying gas removes solvent from the droplets and carries the particles into a collection chamber. In spray drying, factors that can affect yield include, but are not limited to, localized charges on particles (which may promote adhesion of the particles to the spray dryer) and aerodynamics of the particles (which may make it difficult to collect the particles). In general, yield of the spray dry process depends in part on the particle formulation.

The particles are sized such that they can be delivered via an osmotic delivery system of the present invention. Uniform shape and size of the particles typically help to provide a consistent and uniform rate of release from such a delivery system; however, a particle preparation having a non-normal particle size distribution profile may also be used. For example, in the osmotic delivery devices described herein, the size of the particles is less than about 30%, preferably is less than about 20%, preferably is less than about than 10%, and more preferably less than about 5% of the diameter of the delivery (or exit) orifice.

In a preferred embodiment, when the particles are suspended in a vehicle they do not settle in less than about three months at delivery temperature. Generally speaking, smaller particles tend to have a lower settling rate in viscous vehicles than larger particles. Accordingly, micron- to nano-sized particles are typically desirable. In an embodiment of the particle formulation for use with an osmotic delivery system, wherein the delivery orifice diameter of the implant is in a range of, for example, about 0.1 to about 0.5 mm, particle sizes may be preferably less than about 50 microns, more preferably less than about 10 microns, more preferably in a range from about 3 to about 7 microns. In one embodiment, the orifice is about 0.25 mm (about 250 μm) and the particle size is approximately 3-5 μm.

In some aspects of the present invention, a particle formulation comprises one or more polypeptide, one or more stabilizers, and optionally a buffer. The stabilizers may be, for example, carbohydrate, antioxidant, amino acid, buffer, or inorganic compound. In a preferred embodiment, the carbohydrate is a disaccharide (e.g., sucrose), the antioxidant is an amino acid (e.g., methionine), and the buffer is an organic buffer (e.g., citrate). The amounts of stabilizers and buffer in the particle formulation can be determined experimentally based on the activities of the stabilizers and buffers and the desired characteristics of the formulation. Typically, the amount of carbohydrate in the formulation is determined by aggregation concerns. In general, the carbohydrate level is not be too high so as to avoid promoting crystal growth in the presence of water due to excess carbohydrate unbound to the peptide. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize the peptide during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include non-reducing sugars such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, tryptophan, serine, asparagines, cysteine, tyrosine, lysine, and norleucine. Preferred amino acids include those that readily oxidize, e.g., cysteine, methionine, and tryptophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, $NaSCN$, $Na_2SO4$, $NaHCO_3$, KCl, $KH_2PO4$, $CaCl_2$, and $MgCl_2$.

In addition, the particle formulation may include other excipients such as surfactants, bulking agents, and salts. Examples of surfactants include, but are not limited to, Polysorbate 20, Polysorbate 80, PLURONIC® (BASF Corporation, Mount Olive, N.J.) F68, and sodium docecyl sulfate (SDS). Examples of bulking agents include, but are not limited to, mannitol and glycine. Examples of salts include, but are not limited to, sodium chloride, calcium chloride, and magnesium chloride.

2.2.3 Vehicle Formulations

In one aspect of the present invention, a vehicle (e.g., a suspension vehicle) provides a stable environment in which a beneficial agent (e.g., a small molecule and/or polypeptide particles) is dispersed. The vehicle typically comprises one or more polymer and one or more solvent that together form a solution of sufficient viscosity to uniformly suspend the beneficial agent(s). The piston assemblies of the present invention, as described herein above, are substantially impermeable to and substantially resistant to leaching when exposed to the vehicle, particularly to the organic solvent of the vehicle.

The viscosity of the vehicle is typically sufficient to prevent the beneficial agent from settling during storage and use in a method of delivery, for example, in the osmotic delivery devices. The vehicle is biodegradable in that the vehicle disintegrates or breaks down over a period of time in response to a biological environment. The disintegration of the vehicle may occur by one or more physical or chemical degradative processes such as by enzymatic action, oxidation, reduction, hydrolysis (e.g., proteolysis), displacement (e.g., ion exchange), or dissolution by solubilization, emulsion or micelle formation. After the vehicle disintegrates, components of the vehicle are absorbed or otherwise dissipated by the body and surrounding tissue of the subject.

The solvent in which the polymer is dissolved may affect characteristics of the beneficial agent formulation such as the behavior of the beneficial agent formulation during storage. A solvent may be selected in combination with a polymer so that the resulting vehicle exhibits phase separation upon contact with the aqueous environment. Optionally, the solvent may be selected in combination with the polymer so that the resulting vehicle exhibits phase separation upon contact with the aqueous environment having less than approximately about 10% water.

In some embodiments, the solvent may be an acceptable solvent that is not miscible with water. The solvent may also be selected so that the polymer is soluble in the solvent at high concentrations such as at a polymer concentration of greater than about 30%. However, typically the peptide is substantially insoluble in the solvent. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, carboxylic acid esters, fatty acid esters, or mixtures thereof. The solvent used in the vehicle may be "dry," in that it has a low moisture content. Preferred solvents for use in formulation of the vehicle include lauryl lactate, lauryl alcohol, and benzyl benzoate.

Additional solvents that may be useful in the practice of the present invention include, but are not limited to, the following: vegetable oils (sesame oil, cottonseed oil, soybean oil); triglycerides; glycerin; glycerol; polyethylene glycol (e.g., PEG400); glycofurol; N-methylpyrrolidone; polysorbates (e.g., polysorbate 20 and polysorbate 80); alpha-tocopherol (e.g., Vitamin E); dimethyl sulfoxide; sucrose acetate isobutyrate (SAIB); or silicon medical fluid.

Examples of polymers for formulation of the vehicles of the present invention include, but are not limited to, a polyester (e.g., polylactic acid or polylacticpolyglycolic acid), a polymer comprising pyrrolidone (e.g., polyvinylpyrrolidone (PVP) having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. In one embodiment, the polymer is PVP having a molecular weight of 2,000 to 1,000,000. The polymer used in the vehicle may include one or more different polymers or may include different grades of a single polymer. The polymer used in the vehicle may also be dry or have a low moisture content.

Generally speaking, a vehicle according to the present invention may vary in composition based on the desired performance characteristics. In one embodiment, the vehicle may comprise about 25 wt % to about 80 wt % polymer and about 75 wt % to about 20 wt % solvent, more preferably 40 wt % to about 75 wt % polymer and about 60 wt % to about 25 wt % solvent. Preferred embodiments of a vehicle include vehicles formed of polymer and solvent combined at the following ratios: about 75 wt % polymer and about 25 wt % solvent; about 60 wt % polymer and about 40 wt % solvent; about 55 wt % polymer and about 45 wt % solvent; about 50 wt % polymer and about 50 wt % solvent; about 45 wt % polymer and about 55 wt % solvent; about 40 wt % polymer and about 60 wt % solvent; and about 25 wt % polymer and about 75 wt % solvent. In a preferred embodiment the solvent is benzyl benzoate and the polymer is PVP.

The vehicle may exhibit Newtonian behavior. The vehicle is typically formulated to provide a viscosity that maintains a uniform dispersion of the beneficial agent(s) for a predetermined period of time in a beneficial agent formulation. This helps facilitate making a beneficial agent formulation tailored to provide controlled delivery of the peptide at a desired rate. The viscosity of the vehicle may vary depending on the desired application, the size and type of the particle formulation, and the loading of the particle formulation in the vehicle. The viscosity of the vehicle may be varied by altering the type or relative amount of the solvent or polymer used.

The vehicle may have a viscosity ranging from about 100 poise to about 1,000,000 poise, preferably from about 1,000 poise to about 100,000 poise. The viscosity may be measured at 37° C., at a shear rate of $10^{-4}$/sec, using a parallel plate rheometer. In one embodiment, the viscosity of the vehicle ranges from approximately 5,000 poise to approximately 50,000 poise. In one embodiment, the vehicle has a viscosity of about 16,700 poise at 33° C. In preferred embodiments, the viscosity range is between about 12,000 to about 18,000 poise at 33° C.

The vehicle may exhibit phase separation when contacted with the aqueous environment. However, typically the vehicle exhibits substantially no phase separation as a function of temperature. For example, at a temperature ranging from approximately 0° C. to approximately 70° C. and upon temperature cycling, such as cycling from 4° C. to 37° C. to 4° C., the vehicle typically exhibits no phase separation. In some embodiments of the invention, the vehicle exhibits phase separation when contacted with the aqueous environment having less than approximately 10% water.

The vehicle may be, for example, prepared by combining the polymer and the solvent under dry conditions such as in a dry box. The polymer and solvent may be combined at an elevated temperature, for example, from approximately 40°

C. to approximately 70° C., and allowed to liquefy and form the single phase. The ingredients may be blended under vacuum to remove air bubbles produced from the dry ingredients. The ingredients may be combined using a conventional mixer such as a dual helix blade or similar mixer, for example, set at a speed of approximately 40 rpm. However, higher speeds may also be used to mix the ingredients. Once a liquid solution of the ingredients is achieved, the vehicle may be cooled to room temperature. Differential scanning calorimetry (DSC) may be used to verify that the vehicle is a single phase. Further, the components of the vehicle (e.g., the solvent and/or the polymer) may be treated to substantially reduce or substantially remove peroxides (e.g., by treatment with methionine; e.g., U.S. Patent Application Publication No. 2007-0027105).

The beneficial agent(s) (e.g., a small molecule and/or particle formulation) is added to the vehicle to form a beneficial agent formulation. The beneficial agent formulation may be prepared by dispersing the beneficial agent(s) in the vehicle. The vehicle may be heated and the beneficial agent(s) added to the vehicle under dry conditions. The ingredients may be mixed under vacuum at an elevated temperature such as from about 40° C. to about 70° C. The ingredients may be mixed at a sufficient speed such as from about 40 rpm to about 120 rpm, and for a sufficient amount of time, for example, about 15 minutes, to achieve a uniform dispersion of the beneficial agent(s) in the vehicle. The mixer may be a dual helix blade or other suitable mixer. The resulting mixture may be removed from the mixer, sealed in a dry container to prevent water from contaminating the beneficial agent formulation, and allowed to cool to room temperature before further use, for example, loading into an osmotic delivery system.

The beneficial agent formulation typically has an overall moisture content of less than about 10 wt %, preferably less than about 5 wt %, and more preferably less than about 4 wt %.

In summary, the components of the vehicle provide biocompatibility with the subject in whom use is intended. Components of the vehicle offer suitable chemico-physical properties to form stable formulations of beneficial agents. These properties include, but are not limited to, the following: viscosity of the vehicle (which may include the viscosity of the vehicle plus beneficial agent); purity of the vehicle; residual moisture of the vehicle; density of the vehicle; compatibility with the beneficial agent(s); compatibility with implantable devices; molecular weight of the polymer; stability of the vehicle; and hydrophobicity and hydrophilicity of the vehicle. These properties can be manipulated and controlled, for example, by variation of the vehicle composition and manipulation of the ratio of components used in the vehicle.

All components included in the particle formulation are typically acceptable for pharmaceutical use in subjects, particularly humans.

Some additional examples of suitable solvents, polymers, beneficial agents, and particle formulations have been described (e.g., U.S. Pat. Nos. 5,972,370, 5,932,547, 6,730,328, 7,258,869; and U.S. Patent Application Publication Nos. 2004-0224903, 2005-0008661, 2005-0112188, 2006-0193918, 2006-0216242, 2006-0263433, 2006-0251618).

2.2.4 Combined Formulations

In some embodiments of the present invention, a single beneficial agent in a solution or formulation is used to fill a beneficial agent chamber of an osmotic delivery device, for example, two or more osmotic delivery devices, wherein each delivery device has a single beneficial agent chamber, can be used to delivery a single beneficial agent from each osmotic delivery device in order to achieve delivery of two or more beneficial agents. In this case, each osmotic delivery device delivers a solution or suspension formulation comprising a different beneficial agent. In other embodiments of the present invention, a single osmotic delivery device may be employed wherein each device has two or more beneficial agent reservoirs. In this case, a single beneficial agent can be delivered from one beneficial agent chamber, a different beneficial agent from beneficial agent chamber, and so on.

In another aspect the present invention relates to formulations of beneficial agents wherein two or more beneficial agents are provided in combination in a single solution or suspension formulation (i.e., a combined beneficial agent suspension formulation). The present invention relates to methods of making these formulations, the formulations themselves, and use of the formulations in osmotic delivery devices, for example, as described herein. This aspect of the invention provides four basic formulation modifications the description of which follow herein below.

First, two or more beneficial agents may be dissolved directly in the vehicle. Typically, small molecule beneficial agents are most suited to this method of preparing a solution formulation. Small polypeptides are also often suited to this method. An example of such a formulation is providing a dimethylsulfoxide (DMSO)-based vehicle in which a small polypeptide, such as leuprolide acetate, is dissolved along with a second small polypeptide, such as goserelin acetate, wherein both of the small polypeptides are soluble in the vehicle.

Second, one or more beneficial agent may be dissolved in a vehicle and one or more beneficial agent formulated into particles may be suspended in a vehicle. Typically, small molecules and small polypeptides are most suited to be dissolved in the suspension vehicle. Components of suitable particle formulations for a beneficial agent, which are not able to be dissolved in the vehicle, can be selected as described herein above. A beneficial agent may not, for example, be stable in a solution formulation and therefore may need to be stabilized in a particle form for suspension. In one embodiment, a first beneficial agent can be dissolved in the vehicle thus allowing maximum loading of particles that contain a second beneficial agent. By dissolving the first beneficial agent in the vehicle the loading potential of the particle containing the second beneficial agent is typically not diminished. This combination maximizes the amount of the two beneficial agents that can be delivered from an osmotic delivery device with, for example, one beneficial agent reservoir. If the dissolved beneficial agent affects the viscosity of the suspension vehicle, the components of the suspension vehicle can be altered to accommodate the change in viscosity, for example, by increasing or decreasing the amount of a polymer in the vehicle that is used to increase viscosity of the vehicle. An example of such a formulation would be dissolving a small molecule antiviral drug such as Telaprevir (VX-950; Vertex Pharmaceuticals, Inc., Cambridge, Mass.) in the non-aqueous organic solvent-based vehicle, such as lauryl alcohol and povidone, and dispersing particles comprising an interferon, such as an alpha interferon or omega interferon, in the vehicle.

Third, two or more beneficial agents can be combined in one particle formulation. In situations where the beneficial agents (i) can be stabilized in a particle formulation having the same components, and (ii) do not adversely affect each other's stability, then the beneficial agents can be combined in a single particle that can be suspended in a vehicle. For example, this method is suited to the formation of two polypeptides into a single particle formulation, such as, two interferons. Another example is the formulation of two polypeptides into a single particle wherein each of the polypeptides provides a therapeutic benefit for different aspect of a single disease or condition, for example, (i) exendin-4 and oxyntomodulin (Example 4A) or exendin-4 and PYY (Example 4B) for the treatment of diabetes or to facilitate or promote weight loss, or (ii) leptin and amylin to facilitate or promote weight loss, for example, in obese or overweight subjects. Another example is the formulation of two or more polypeptides into a single particle wherein each of the polypeptides provides a therapeutic benefit for different aspect of a single disease or condition, for example, (i) exendin-4, oxyntomodulin, and PYY for the treatment of diabetes or to facilitate or promote weight loss, (ii) leptin and amylin and PYY to facilitate or promote weight loss, for example, in obese or overweight subjects.

Fourth, two or more beneficial agents can be formulated individually into different particle formulations. The components of the particle formulations, other than the beneficial agent, may be the same or different. The different particle formulation can then be suspended in the same suspension vehicle, thus providing a single suspension formulation comprising two different particle formulations, wherein each particle formulation has different beneficial agents. For example, this method is suited to the formation of two polypeptides each in a different particle formulation, such as, exendin-4 in one particle formulation, and oxyntomodulin or PYY in a second particle formulation, wherein the two particle formulations are combined in a single suspension formulation and administered to facilitate or promote weight loss, for example, in obese or overweight subjects. As another example, this method is suited to the formation of two polypeptides each in a different particle formulation, such as, leptin in one particle formulation, and amylin in a second particle formulation, wherein the two particle formulations are combined in a single suspension formulation and administered to facilitate or promote weight loss. One advantage of preparing particle formulations comprising single beneficial agents is that the relative proportions of the different particle formulations can be varied to maximize therapeutic effect of the different beneficial agents. For example, the amount of a particle formulation with a first beneficial agent may be greater than, equal to, or less than the amount of the particle formulation with a second beneficial agent in a suspension formulation comprising both of the particle formulations. An example is the formulation of two or more polypeptides into two or more particles wherein each of the polypeptides provides a therapeutic benefit for different aspect of a single disease or condition, for example, (i) exendin-4 in a first particle formulation and oxyntomodulin or PYY in a second particle formulation, the particle formulations combined in a single suspension vehicle for the treatment of diabetes or to facilitate or promote weight loss, (ii) exendin-4 in a first particle formulation, oxyntomodulin in the first particle formulation, and PYY in a second particle formulation, the particle formulations combined in a single suspension vehicle administered to facilitate or promote weight loss, for example, in obese or overweight subjects, (iii) leptin in a first particle formulation and amylin in a second particle formulation, the particle formulations combined in a single suspension vehicle administered to facilitate or promote weight loss, or (iv) leptin in a first particle formulation, amylin in the first particle formulation, and PYY in a second particle formulation, the particle formulations combined in a single suspension vehicle administered to facilitate or promote weight loss.

These four modifications can also be combined, for example, one or more beneficial agent may be soluble in the vehicle and this may be combined with a particle formulation suspended in the vehicle, wherein the particle formulation comprises two or more beneficial agents. In addition to the examples given above, some further examples of combinations that may be employed in one or more of the above-described combined formulations include, but are not limited to, the following: (i) combining a Her-2 blocker (e,g, lapatinib, which is a small molecule) and a platelet-derived growth factor blocker (e.g., imatinib) together in a formulation to treat her-2 sensitive tumors; (ii) combining a small antibody fragment directed against vascular endothelial growth factor with an antibody fragment directed Her-2 to treat her-2 sensitive tumors; and (iii) combining ribavirin with an interferon (e.g., omega interferon) for the treatment of viral disease (e.g., hepatitis C virus infection).

Suitable components for vehicles (e.g., solvents and polymers), beneficial agents, and components for particle formulations (e.g., carbohydrate, antioxidants, amino acids, and buffers) have been described herein above.

The present invention also includes methods of manufacturing the formulations of the present invention, including the particle formulations, vehicles, and beneficial agent formulations (including, but not limited to suspension formulations) described herein above.

2.3 Examples of Administration of Multiple Beneficial Agents for Treating Diseases or Conditions As discussed herein above, the administration of multiple beneficial agents can be accomplished by several approaches including, for example, (i) delivery of combined formulations of the beneficial agents from an osmotic delivery device with a single beneficial agent chamber, (ii) delivery of individual formulations of each beneficial agent from individual osmotic delivery devices each having a single beneficial agent chamber, (iii) delivery of individual formulations of each beneficial agent from an osmotic delivery device having a beneficial agent chamber for each beneficial agent formulation, or (iv) delivery of combined formulations of beneficial agents from an osmotic delivery device having a beneficial agent chamber for each combined beneficial agent formulation.

Typically, an osmotic delivery device is implanted within the subject, for example, subcutaneously. The device(s) can be inserted subcutaneously into either or both arms (e.g., in the inside, outside, or back of the upper arm) or the abdomen. Preferred locations in the abdomen are under the abdominal skin in the area extending below the ribs and above the belt line. To provide a number of locations for insertion of one or more osmotic delivery device within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions.

Following here are several examples of how the osmotic delivery devices and formulations of the present invention may be combined to treat a selected disease or condition.

In one embodiment, the formulations and osmotic delivery devices of the present invention can be administered to facilitate or promote weight loss, for example, in obese or overweight subjects. The present invention provides methods of treating or preventing disorders or conditions associated with an undesirable level of a satiety factor by administering to a subject in need thereof an effective amount of an agonist or antagonist of a satiety factor. Exemplary disorders or conditions associated with an undesirable level of a satiety factor include overweight, obesity, metabolic disorders, hypertension, lipid related disorders, anorexia and type II diabetes.

Administration of amylin appears to restore leptin responsivity in obesity (e.g., J. Roth, et al., 66th Annual Scientific Sessions of the American Diabetes Association (ADA), Washington, D.C., abstract number 52-LB). Accordingly, co-administration of leptin with amylin may provide a useful treatment of obesity by, for example, reduction of body weight and/or body fat in treated subjects, as well facilitating or promoting weight loss, for example, in overweight subjects.

The formulations and osmotic delivery devices of the present invention may be employed to treat Type II diabetes and/or facilitate or promote weight loss, for example, in obese or overweight subjects, in a number of ways. A few examples, in view of the teachings presented herein, are as follows. First, a particle formulation comprising amylin (e.g., pramlintide acetate) is prepared and a particle formulation comprising leptin is prepared. Each particle formulation may, for example, comprise, a carbohydrate (e.g., sucrose), an antioxidant (e.g., methionine), and a buffer (e.g., citrate) in addition to the beneficial agent. Each particle formulation is suspended in a vehicle (for example, comprising benzyl benzoate and polyvinylpyrrolidone). Each of the suspensions is loaded into an osmotic delivery device (e.g., as shown in FIG. 1), wherein the osmotic delivery device has a single beneficial agent chamber. Thus two osmotic delivery devices are provided, one loaded with a suspension formulation comprising amylin and one loaded with a suspension formulation comprising leptin. The two osmotic delivery devices are then implanted in a subject to facilitate or promote weight loss, for example, in an obese or overweight subject in need of treatment.

Second, an exendin-4 particle formulation (Example 1) and an oxyntomodulin particle formulation (Example 2) are each dispersed in a vehicle to provide a suspension formulation (Example 7A). The suspension formulation is then loaded into the beneficial agent chamber of an osmotic delivery device, for example, the device illustrated in FIG. 1, chamber 16.

Third, an exendin-4 particle formulation (Example 1) and PYY particle formulation (Example 3) are each dispersed throughout a vehicle to provide a suspension formulation (Example 7B). The suspension formulation is then loaded into the beneficial agent chamber of an osmotic delivery device, for example, the device illustrated in FIG. 1, chamber 16.

In an alternate embodiment, a particle formulation comprising two or more beneficial agents is prepared. In one example, two beneficial agents are amylin and leptin. The particle formulation may, for example, comprise, a carbohydrate (e.g., sucrose), an antioxidant (e.g., methionine), and a buffer (e.g., citrate) in addition to the beneficial agents. The particle formulation is suspended in a vehicle (for example, comprising benzyl benzoate and polyvinylpyrrolidone). The suspensions is loaded into an osmotic delivery device (e.g., as shown in FIG. 1), wherein the osmotic delivery device has a single beneficial agent chamber. Thus a single osmotic delivery device is provided loaded with a suspension formulation comprising amylin and leptin. The osmotic delivery device is then implanted in a subject.

As a second example, a single particle formulation comprising both exendin and oxyntomodulin (Example 4A) is dispersed throughout a vehicle to provide a suspension formulation (Example 7C). The suspension formulation is then loaded into the beneficial agent chamber of an osmotic delivery device, for example, the device illustrated in FIG. 1, chamber 16.

As a third example, a single particle formulation comprising exendin-4 and PYY (Example 4B) is dispersed throughout a vehicle to provide a suspension formulation (Example 7D). The suspension formulation is then loaded into the beneficial agent chamber of an osmotic delivery device, for example, the device illustrated in FIG. 1, chamber 16.

In another embodiment, each of the suspension formulations just described are loaded into one osmotic delivery device having multiple, for example, two beneficial agent chambers wherein one suspension formulation is loaded into one beneficial agent chamber. As a first example, a single osmotic delivery device is provided wherein one beneficial agent chamber is loaded with a suspension formulation comprising amylin and the other beneficial agent chamber is loaded with a suspension formulation comprising leptin.

As a second example, an exendin-4 particle formulation (Example 1) is dispersed throughout a vehicle to provide a suspension formulation. The suspension formulation is then loaded into a first beneficial agent chamber of an osmotic delivery device, for example, as described in FIG. 3, chamber 330 (Example 8A). An oxyntomodulin particle formulation (Example 2) is dispersed throughout the vehicle to provide a suspension formulation. The suspension formulation is then loaded into a second beneficial agent chamber of an osmotic delivery device, for example, as described in FIG. 3, chamber 340 (Example 8A). A PYY particle formulation (Example 3) is dispersed throughout a vehicle to provide a suspension formulation. The suspension formulation is then loaded into a third beneficial agent chamber of an osmotic delivery device, for example, as described in FIG. 3, chamber 350 (Example 8A).

As a third example, an alpha interferon particle formulation (Example 5) is dispersed throughout a vehicle to provide a suspension formulation. The suspension formulation is then loaded into a first beneficial agent chamber of an osmotic delivery device, for example, as described in FIG. 4, chamber 450 (Example 8B). An Amphotericin B solution formulation (Example 6A) is then loaded into a second beneficial agent chamber of an osmotic delivery device, for example, as described in FIG. 4, chamber 460 (Example 8B).

As a fourth example, an alpha interferon particle formulation (Example 5) is dispersed throughout a vehicle to provide a suspension formulation. The suspension formulation is then loaded into a first beneficial agent chamber of an osmotic delivery device, for example, as described in FIG. 4, chamber 450 (Example 8C). An Amphotericin B formulation (Example 6B) is then loaded into a second beneficial agent chamber of an osmotic delivery device, for example, as described in FIG. 4, chamber 460 (Example 8C).

Numerous examples of osmotic delivery devices having two beneficial agent chambers are provided herein (e.g., FIG. 4A, FIG. 5A, FIG. 6, and FIG. 7A). The single osmotic delivery device is then implanted in a subject to achieve treatment of a disease or condition.

Many disease or conditions are suitable for treatment using the beneficial agent formulations (e.g., suspension formulations) and osmotic delivery devices of the present invention, wherein the goal is to provide a treatment comprising two or more beneficial agents. The two or more beneficial agents may be used to treat the same disease or condition (e.g., diabetes) or different diseases or conditions (e.g., obesity and diabetes). In Table 1 a number of disease and conditions are listed and, provided in the adjacent column to the disease or condition are proposed beneficial agents for treatment of the disease or condition. The listed beneficial agents include the listed beneficial agents as well as analogs, variants, and derivatives thereof. Typically for the practice of the present invention, two or more beneficial agents are selected for administration to a subject in need of treatment, wherein the two or more beneficial agents are formulated as described herein and administered using the osmotic delivery devices described herein.

TABLE 1

| Disease or Condition | A treatment comprising administration of two or more beneficial agents selected from the following group: |
|---|---|
| Obesity/Diabetes | Ghrelin antagonists, PYY, Leptin, Obestatin, GLP-1, Exendin, Amylin, G protein coupled receptor GRP 119 agonists, selective Melanin Concentrating Hormone (MCH) receptor blockers, Cannabinoid-1 agonists, Lipase inhibitors, Neuropeptide Y (NPY) blocker, Oxymodulin, Silent Mating Type Information Regulation 2 homolog-1 (SIRT-1/sirtuin) activators, Oxyntomodulin, Cholecystokinin (CCK) agonists, Gastric Inhibitory Polypeptide (GIP) agonists |
| Hepatitis | interferons; protease inhibitors, e.g., Telaprevir (VX-950; Vertex Pharmaceuticals, Inc.); antibodies (e.g., monoclonal, humanized, polyclonal, single-chain) |
| Alzheimer's disease | secretase inhibitor, gamma secretase inhibitor, gamma secretase modulators, alpha secretase stimulators, serotonin inhibitors |
| Alzheimer's disease | Metal protein attenuation compounds, Ion channel blockers, Oligomeric amyloid beta formation inhibitors |
| Alzheimer's disease | RAGE inhibitors (Receptor for Advance Glycation endproducts), Antibodies targeting amyloid beta |
| Alzheimer's disease | GSK-3B Kinase inhibitors, Cdk5/p25 Kinase inhibitors, Extracellular signal-regulated kinase 2 (ERK2) inhibitors, C-abl Kinase inhibitors, MARK Kinase inhibitors, Protein phosphate promoters (PP-2A) |
| Alzheimer's disease | Modulators of Amyloid beta production (e.g., secretase inhibitor, gamma secretase inhibitor, gamma secretase modulators, or alpha secretase stimulators), Inhibitors of inhibit amyloid beta aggregation (e.g., Metal protein attenuation compounds, Ion channel blockers, or Oligomeric amyloid beta formation inhibitors), Amyloid beta load reducer (e.g., RAGE inhibitors (Receptor for Advance Glycation endproducts), or Antibodies targeting amyloid beta), Tau-related microtubule destabilization inhibitors (GSK-3B Kinase inhibitors, Cdk5/p25 Kinase inhibitors, ERK2 Kinase inhibitors, C-abl Kinase inhibitors, MARK Kinase inhibitors, Protein phosphate promoters (PP-2A)) |
| Bone Fractures | Receptor activator of NF-κB ligand (RANKL) activators, Bone Morphogenetic Protein-7 (BMP-7) |
| Bone loss during cancer treatment | (RANKL activator and Bisphosphonates) and (Aromatase inhibitors for breast cancer OR Anti-androgens for prostate cancer OR luteinizing hormone-releasing hormone (LHRH) agonists for prostate cancer) |
| Rheumatoid Arthritis | An anti-CD 20 agent, a JAK3 (janus kinase 3) inhibitor, a CCR1 (chemokine [c-c motif] receptor 1) antagonist, a Syk (spleen tyrosine kinase) inhibitor, a P38 MAP kinase inhibitor, CTLA-4 (cytotoxic T-lymphocyte antigen 4), a Tumor necrosis factor (TNF)-alpha antagonist, a TNF-alpha ligand, a steroid, an inhibitor of the IL-12 Superfamily of cytokines (IL-1, 6, 12, 15, 17, 18, 32) |
| Cancer | (Vascular endothelial growth factor (VEGF) blocker or VEGF receptor ligand), (Platelet-derived growth factor (PDGF) blocker or PDGF receptor ligand), a receptor tyrosine kinase inhibiting (rtki) compound |
| Cancer | (a RAS kinase inhibitor or a RAF kinase inhibitor or a MEK kinase inhibitor or an ERK kinase inhibitor) and (an AKT kinase inhibitor or an inhibitor of the mammalian target of rapamycin (mTOR) kinase or S6k1 or 4E-BP1) |
| Cancer | An angiogenesis inhibitor (e.g., VEGF blocker, VEGF receptor ligand, PDGF blocker, PDGF receptor ligand, EGF blocker, a receptor tyrosine kinase inhibiting (rtki) compound), a tumor cell pathway inhibitor (e.g., a RAS kinase inhibitor or a RAF kinase inhibitor or a MEK kinase inhibitor, an ERK kinase inhibitor, a RAS kinase inhibitor or a RAF kinase inhibitor or a MEK kinase inhibitor, an ERK kinase inhibitor), inhibitors of chromatin modification (e.g., an inhibitor of Histone Deacetylase (HDAC), an inhibitor of histone acetyltransferase (HAT)) |
| Cancer | A TNF-alpha antagonist, a TNF-related apoptosis inducing ligand (TRAIL) antibody |
| Cancer | A Wnt inhibitor, a Hh (hedgehog) inhibitor |
| Cancer | A PI-3 Kinase inhibitor, a MEK kinase inhibitor |
| Cancer | A PI-3 Kinase inhibitor, an mTOR kinase inhibitor |
| Cancer | An epidermal growth factor receptor tyrosine kinase inhibitor (EGFr-TKI), a B-cell leukemia/lymphoma 2 (BCL-2) blocker |

TABLE 1-continued

| Disease or Condition | A treatment comprising administration of two or more beneficial agents selected from the following group: |
|---|---|
| Cancer | TRAIL receptor antibody, a traditional cytotoxic compound |
| Cancer | A P38 MAP kinase inhibitor and (a Raf kinase inhibitor, a MEK kinase inhibitor, or an ERK kinase inhibitors) |
| Cancer | A EGFr TKI, an ERB2 inhibitor |

The above-described treatments can be coupled to other treatments as well, for example, to oral, parenteral injection (e.g., subcutaneous, intramuscular, intraorbital, intracapsular, intraspinal, intrasternal, intravenous, intraperitoneal), bolus, infusion, or other administration methods. An example of a co-administered treatment method is the use of traditional cytotoxics for chemotherapy during cancer treatment with two or more beneficial agents that are administered using the formulations and devices described herein. Another example is the co-administration of acetycholinesterase inhibitors and/or N-methyl-D-aspartic acid (NMDA) receptor antagonists for the treatment of Alzheimer's disease with two or more beneficial agents that are administered using the formulation and devices described herein.

EXPERIMENTAL

The following examples are put forth so as to provide those of ordinary skill in the art with a complete disclosure and description of how to make and use the devices, methods, and formulae of the present invention, and are not intended to limit the scope of what the inventor regards as the invention. Efforts have been made to ensure accuracy with respect to numbers used (e.g., amounts, temperature, etc.) but some experimental errors and deviations should be accounted for. Accordingly, specific values are typical approximate values unless otherwise indicated. Unless indicated otherwise, parts are parts by weight, molecular weight is weight average molecular weight, temperature is in degrees Centigrade, and pressure is at or near atmospheric.

The compositions produced according to the present invention meet the specifications for content and purity required of pharmaceutical products.

Example 1

Exendin-4 Particle Formulation

This example describes making an exendin-4 particle formulation. Exendin-4 (0.25 g) was dissolved in 50 mM sodium citrate buffer at pH 6.0. The solution was dialyzed with a formulation solution containing sodium citrate buffer, sucrose, and methionine. The formulated solution was then spray dried using Buchi 290 with 0.7 mm nozzle, outlet temperature of 75° C., atomization pressure of 100 Psi, solid content of 2%, and flow rate of 2.8 mL/min. The dry powder contained 21.5 wt % of exendin-4 with 4.7% residual moisture and 0.228 g/ml density. The ratio of the components in this particle formulation is as follows: approximately 1.1:1:1:2 (exendin-4: methionine: sucrose: citrate buffer).

This exendin-4 dry powder particle formulation provides an example of a beneficial agent for use in the formulations, devices, and methods of the present invention.

Example 2

Oxyntomodulin Particle Formulation

This example describes making an oxyntomodulin particle formulation. Oxyntomodulin (1 g) is dissolved in 50 mM sodium citrate buffer at pH 6.0. The solution is dialyzed with a formulation solution containing sodium citrate buffer, sucrose, and methionine. The formulated solution is then spray dried using Buchi 290 with 0.7 mm nozzle, outlet temperature of 80° C., atomization pressure of 100 Psi, solid content of 2%, and flow rate of 2.5 mL/min. The dry powder contains 25% of Oxyntomodulin. The ratio of the components in this particle formulation is as follows: approximately 1.35:1:1:2 (Oxyntomodulin:methionine:sucrose:citrate buffer).

This oxyntomodulin dry powder particle formulation provides an example of a beneficial agent for use in the formulations, devices, and methods of the present invention.

Example 3

Particle Formulation of Gut Hormone Fragment PYY

This example describes making a PYY particle formulation, wherein the PYY peptide is the $PYY_{3-36}$ variant. PYY (1 g) is dissolved in 50 mM sodium citrate buffer at pH 6.0. The solution is dialyzed with a formulation solution containing sodium citrate buffer, sucrose, and methionine. The formulated solution is then spray dried using Buchi 290 with 0.7 mm nozzle, outlet temperature of 80° C., atomization pressure of 100 Psi, solid content of 2%, and flow rate of 2.5 mL/min. The dry powder contains 25% of PYY. The ratio of the components in this particle formulation is as follows: approximately 1.35:1:1:2 (PYY: methionine: sucrose: citrate buffer).

This PYY dry powder particle formulation provides an example of a beneficial agent for use in the formulations, devices, and methods of the present invention.

Example 4

Multiple Beneficial Agent Particle Formulation

This example describes making particle formulations that each comprise multiple beneficial agents, for example, using exendin-4, oxyntomdulin, and PYY at a predetermined ratios.

A. A Dry Powder Particle Formulation Comprising Exendin-4 and Oxyntomodulin.

Exendin-4 (0.5 g) is dissolved in 25 mM sodium citrate buffer at pH 6.0. The solution is dialyzed with a formulation solution containing sodium citrate buffer, sucrose, and methionine. Oxyntomodulin (2.5 g) is dissolved in 25 mM sodium citrate buffer at pH 6.0. The solution is dialyzed with a formulation solution containing sodium citrate buffer, sucrose, and methionine. The formulated Exendin-4 solution and Oxyntomodulin solution are then mixed together at an Exendin-4/Oxyntomodulin ratio of 1:5. The solution is spray dried using Buchi 290 with 0.7 mm nozzle, outlet temperature of 80° C., atomization pressure of 100 Psi, solid content of 2%, and flow rate of 2.5 mL/min. The dry powder contains 5% of Exendin-4 and 25% of Oxyntomodulin. The ratio of the components in this particle formulation is as follows: approximately 0.3:1.4:1:1:2 (Exendin-4: Oxyntomodulin: methionine: sucrose: citrate buffer).

B. A Dry Powder Particle Formulation Comprising Exendin-4 and PYY.

Exendin-4 (0.5 g) is dissolved in 25 mM sodium citrate buffer at pH 6.0. The solution is dialyzed with a formulation solution containing sodium citrate buffer, sucrose, and methionine. PYY (2.5 g), wherein the PYY peptide is the $PYY_{3-36}$ variant, is dissolved in 25 mM sodium citrate buffer at pH 6.0. The solution is dialyzed with a formulation solution containing sodium citrate buffer, sucrose, and methionine. The formulated Exendin-4 solution and PYY solution are then mixed together at an Exendin-4/PYY ratio of 1:5. The solution is spray dried using Buchi 290 with 0.7 mm nozzle, outlet temperature of 80° C., atomization pressure of 100 Psi, solid content of 2%, and flow rate of 2.5 mL/min. The dry powder contains 5% of Exendin-4 and 25% of PYY. The ratio of the components in this particle formulation is as follows: approximately 0.3:1.4:1:1:2 (Exendin-4: PYY: methionine: sucrose: citrate buffer).

This example demonstrates the formation of particle formulations comprising at least two beneficial agents.

Example 5

Interferon Particle Formulation

This example describes making an alpha interferon particle formulation. Alpha interferon (0.5 g) is dissolved in 50 mM sodium citrate buffer at pH 6.0. The solution is dialyzed with a formulation solution containing sodium citrate buffer, sucrose, and methionine. The formulated solution is then spray dried using Buchi 290 with 0.7 mm nozzle, outlet temperature of 80° C., atomization pressure of 100 Psi, solid content of 2%, and flow rate of 2.5 mL/min. The dry powder contains 20% of the alpha interferon. The ratio of the components in this particle formulation is as follows: approximately 1.1:1:1:2 (interferon: methionine: sucrose: citrate buffer).

This interferon dry powder particle formulation provides an example of a beneficial agent for use in the formulations, devices, and methods of the present invention.

Example 6

Formulations of Amphotericin B

This example describes making two Amphotericin B formulations.

A. Amphotericin B in Single Solvent Vehicle.

Amphotericin B (350 mg) is transferred into a 10 mL volumetric flask. Dimethyl sulfoxide (DMSO) is added to form an Amphotericin B solution having a concentration of 35 mg/mL.

This Amphotericin B solution formulation provides an example of a small molecule beneficial agent for use in the formulations, devices, and methods of the present invention.

B. Amphotericin B in Solvent/Polymer Vehicle.

A vehicle is prepared containing the polymer polyvinylpyrrolidone dissolved in the solvent benzyl benzoate at approximately a 50/50 ratio by weight. The vehicle viscosity is approximately 15,000 poise when measured at 33° C. Amphotericin B is dispersed throughout the vehicle at a concentration of 10% by weight.

This Amphotericin B formulation provides an example of a small molecule beneficial agent for use in the formulations, devices, and methods of the present invention.

Example 7

Multiple Beneficial Agents in Osmotic Delivery Devices

This example describes a number of combinations of multiple beneficial agents, wherein the beneficial agents are delivered from an osmotic delivery device comprising a single beneficial agent chamber.

A. Single Osmotic Delivery Device with Two Particle Formulations.

A vehicle contains the polymer polyvinylpyrrolidone dissolved in the solvent benzyl benzoate at approximately a 50/50 ratio by weight. The vehicle viscosity is approximately 15,000 poise when measured at 33° C. Exendin-4 particle formulation from Example 1 (exendin-4 dry particles) and oxyntomodulin particle formulation from Example 2 (oxyntomodulin dry particles) are dispersed throughout the vehicle at a concentration of 10% particles (1:1 for exendin-4 dry particles and Oxyntomodulin dry particles) by weight to provide a suspension formulation. The suspension formulation is then loaded into the beneficial agent chamber of an osmotic delivery device, such as the device illustrated in FIG. 1, chamber 16. The osmotic delivery device is capable of providing delivery of these two beneficial agents continuously.

B. Single Osmotic Delivery Device with Two Particle Formulations.

A vehicle contains the polymer polyvinylpyrrolidone dissolved in the solvent benzyl benzoate at approximately a 50/50 ratio by weight. The vehicle viscosity is approximately 15,000 poise when measured at 33° C. Exendin-4 particle formulation from Example 1 (exendin-4 dry particles) and PYY particle formulation from Example 3 (PYY dry particles) are dispersed throughout the vehicle at a concentration of 10% particles (1:1 for exendin-4 dry particles and PYY dry particles) by weight to provide a suspension formulation. The suspension formulation is then loaded into the beneficial agent chamber of an osmotic delivery device, such as the device illustrated in FIG. 1, chamber 16. The osmotic delivery device is capable of providing delivery of these two beneficial agents continuously.

C. Single Osmotic Delivery Device with One Particle Formulation Having Two Beneficial Agents.

A vehicle contains the polymer polyvinylpyrrolidone dissolved in the solvent benzyl benzoate at approximately a 50/50 ratio by weight. The vehicle viscosity is approximately 15,000 poise when measured at 33° C. Particles from Example 4A containing 5% exendin-4 and 25% oxyntomodulin are dispersed throughout the vehicle at a concentration of 10% particles by weight to provide a suspension formulation. The suspension formulation is then loaded into the beneficial agent chamber of an osmotic delivery device, such as, the device illustrated in FIG. 1, chamber 16. The osmotic delivery device is capable of providing delivery of these two beneficial agents continuously.

D. Single Osmotic Delivery Device with One Particle Formulation Having Two Beneficial Agents.

A vehicle contains the polymer polyvinylpyrrolidone dissolved in the solvent benzyl benzoate at approximately a 50/50 ratio by weight. The vehicle viscosity is approximately 15,000 poise when measured at 33° C. Particles from Example 4B containing 5% exendin-4 and 25% PYY are dispersed throughout the vehicle at a concentration of 10% particles by weight to provide a suspension formulation. The suspension formulation is then loaded into the beneficial agent chamber of an osmotic delivery device, such as, the device illustrated in FIG. 1, chamber 16. The osmotic delivery device is capable of providing delivery of these two beneficial agents continuously.

Example 8

Multiple Beneficial Agents in Osmotic Delivery Devices Comprising Multiple Beneficial Agent Chambers This example describes a number of combinations of multiple beneficial agents, wherein the beneficial agents are delivered from an osmotic delivery device comprising more than one beneficial agent chamber.

A. Single Osmotic Delivery Device with Three Beneficial Agent Chambers.

A vehicle containing the polymer polyvinylpyrrolidone is dissolved in the solvent benzyl benzoate at approximately a 50/50 ratio by weight. The vehicle viscosity is approximately 15,000 poise when measured at 33° C.

Exendin-4 particle formulation from Example 1 (exendin-4 dry particles) is dispersed throughout the vehicle at a concentration of 10% particles by weight to provide a suspension formulation. The suspension formulation is then loaded into a first beneficial agent chamber of an osmotic delivery device, such as described in FIG. 3, chamber 330.

Oxyntomodulin particle formulation from Example 2 (oxyntomodulin dry particles) is dispersed throughout the vehicle at a concentration of 10% particles by weight to provide a suspension formulation. The suspension formulation is then loaded into a second beneficial agent chamber of an osmotic delivery device, such as described in FIG. 3, chamber 340.

PYY particle formulation from Example 3 (PYY dry particles) is dispersed throughout the vehicle at a concentration of 10% particles by weight to provide a suspension formulation. The suspension formulation is then loaded into a third beneficial agent chamber of an osmotic delivery device, such as described in FIG. 3, chamber 350. The osmotic delivery device is capable of providing delivery of these three beneficial agents continuously.

B. Single Osmotic Delivery Device with Two Beneficial Agent Chambers.

Alpha interferon particle formulation from Example 5 (interferon dry particles) is dispersed throughout a vehicle at a concentration of 10% particles by weight to provide a suspension formulation. The vehicle contains the polymer polyvinylpyrrolidone dissolved in the solvent benzyl benzoate at approximately a 50/50 ratio by weight. The vehicle viscosity is approximately 15,000 poise when measured at 33° C. The suspension formulation is then loaded into a first beneficial agent chamber of an osmotic delivery device, such as described in FIG. 4, chamber 450.

Amphotericin B solution formulation from Example 6A is then loaded into a second beneficial agent chamber of an osmotic delivery device, such as described in FIG. 4, chamber 460. The osmotic delivery device is capable of providing delivery of these two beneficial agents continuously.

C. Single Osmotic Delivery Device with Two Beneficial Agent Chambers.

Alpha interferon particle formulation from Example 5 (interferon dry particles) is dispersed throughout a vehicle at a concentration of 10% particles by weight to provide a suspension formulation. The vehicle contains the polymer polyvinylpyrrolidone dissolved in the solvent benzyl benzoate at approximately a 50/50 ratio by weight. The vehicle viscosity is approximately 15,000 poise when measured at 33° C. The vehicle viscosity is approximately 15,000 poise when measured at 33° C. The suspension formulation is then loaded into a first beneficial agent chamber of an osmotic delivery device, such as described in FIG. 4, chamber 450.

Amphotericin B formulation from Example 6B, Amphotericin B in polyvinylpyrrolidone/benzyl benzoate, is then loaded into a second beneficial agent chamber of an osmotic delivery device, such as described in FIG. 4, chamber 460. The osmotic delivery device is capable of providing delivery of these two beneficial agents continuously.

As is apparent to one of skill in the art, various modification and variations of the above embodiments can be made without departing from the spirit and scope of this invention. Such modifications and variations are within the scope of this invention.

The invention claimed is:

1. An osmotic delivery device comprising:
a beneficial agent formulation comprising (i) a non-aqueous, viscous vehicle comprising a solvent and a polymer, the vehicle having a viscosity of between about 12,000 to about 18,000 poise at 33° C., and (ii) a particle formulation comprising two or more polypeptides, wherein the two or more polypeptides are selected from the group consisting of GLP-1, exendin-4, PYY, and oxyntomodulin; wherein the particle formulation is suspended in the non-aqueous, viscous vehicle.

2. The device of claim 1, wherein the two or more polypeptides are formulated into one particle formulation that is suspended in the vehicle.

3. The device of claim 2, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, and (ii) the polypeptides are exendin-4 and oxyntomodulin, and the particle formulation further comprises sucrose, methionine, and citrate buffer.

4. The device of claim 2, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, and (ii) the polypeptides are exendin-4 and PYY, and the particle formulation further comprises sucrose, methionine, and citrate buffer.

5. The device of claim 2, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, and (ii) the polypeptides are GLP-1 and oxyntomodulin, and the particle formulation further comprises sucrose, methionine, and citrate buffer.

6. The device of claim 2, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, and (ii) the polypeptides are GLP-1 and oxyntomodulin, and the particle formulation further comprises sucrose, methionine, and citrate buffer.

7. The device of claim 1, wherein a first polypeptide is formulated into a first particle formulation and a second polypeptide is formulated into a second particle formulation, and the first and second particle formulations are suspended in the vehicle.

8. The device of claim 7, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, (ii) the first polypeptide is exendin-4 and the first particle formulation further comprises sucrose, methionine, and citrate buffer, and (iii) the second polypeptide is oxyntomodulin and the second particle formulation further comprises sucrose, methionine, and citrate buffer.

9. The device of claim 7, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, (ii) the first polypeptide is exendin-4 and the first particle formulation further comprises sucrose, methionine, and citrate buffer, and (iii) the second polypeptide is PYY and the second particle formulation further comprises sucrose, methionine, and citrate buffer.

10. The device of claim 7, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, (ii) the first polypeptide is GLP-1 and the first particle formulation further comprises sucrose, methionine, and citrate buffer, and (iii) the second polypeptide is oxyntomodulin and the second particle formulation further comprises sucrose, methionine, and citrate buffer.

11. The device of claim 7, wherein (i) the solvent is benzyl benzoate and the polymer is polyvinylpyrrolidone, and the vehicle comprises about 25 wt % to about 80 wt % polyvinylpyrrolidone and about 75 wt % to about 20 wt % benzyl benzoate, (ii) the first polypeptide is GLP-1 and the first particle formulation further comprises sucrose, methionine, and citrate buffer, and (iii) the second polypeptide is PYY and the second particle formulation further comprises sucrose, methionine, and citrate buffer.

12. The device of claim 1, wherein first polypeptide is exendin-4 and a second polypeptide is oxyntomodulin.

13. The device of claim 1, wherein a first polypeptide is exendin-4 and a second polypeptide is PYY.

14. A method of treating a disease or condition in a subject in need of treatment, comprising:
providing the osmotic delivery device of claim 1 to the subject, wherein (i) the osmotic delivery device delivers a therapeutically effective amount of two or more polypeptides to treat the disease or condition, and (ii) the disease or condition is selected from the group consisting of type II diabetes, overweight, and obesity.

15. The method of claim 14, wherein (i) a first polypeptide is exendin-4, and a second polypeptide is oxyntomodulin or PYY; and (ii) the two polypeptides are formulated into one particle formulation that is suspended in the vehicle or the first polypeptide is formulated into a first particle formulation and the second polypeptide is formulated into a second particle formulation and the first and second particle formulations are suspended in the vehicle.

16. The method of claim 14, wherein (i) a first polypeptide is GLP-1, and a second polypeptide is oxyntomodulin or PYY; and (ii) the two polypeptides are formulated into one particle formulation that is suspended in the vehicle or the first polypeptide is formulated into a first particle formulation and the second polypeptide is formulated into a second particle formulation and the first and second particle formulations are suspended in the vehicle.

17. The device of claim 1, wherein a first polypeptide is PYY, and a second polypeptide is oxyntomodulin.

18. The device of claim 1, wherein a first polypeptide is exendin-4, a second polypeptide is oxyntomodulin, and a third polypeptide is PYY.

19. The device of claim 1, wherein a first polypeptide is GLP-1, a second polypeptide is oxyntomodulin, and a third polypeptide is PYY.

20. The device of claim 1, wherein the solvent is selected from the group consisting of lauryl lactate, lauryl alcohol, and benzyl benzoate.

21. The device of claim 20, wherein the polymer is polyvinylpyrrolidone.

22. The device of claim 1, wherein the polymer is polyvinylpyrrolidone.

23. The device of claim 1, wherein the solvent is benzyl benzoate and the polymer is polyvinylpyrrolidone.

24. The device of claim 1, wherein the vehicle comprises about 25 wt % to about 80 wt % polymer and about 75 wt % to about 20 wt % solvent.

25. The device of claim 1, wherein the particle formulation comprises a carbohydrate, an antioxidant, and a buffer.

26. The device of claim 25, wherein the carbohydrate is a non-reducing sugar, the antioxidant is an amino acid, and the buffer is an organic buffer.

27. The device of claim 26, wherein the non-reducing sugar is selected from the group consisting of sucrose, trehalose, and raffinose.

28. The device of claim 26, wherein the amino acid is selected from the group consisting of cysteine, methionine, and tryptophan.

29. The device of claim 26, wherein the organic buffer is selected from the group consisting of citrate, histidine, succinate, and tris.

30. The device of claim 1, wherein a first polypeptide is GLP-1 and a second polypeptide is oxyntomodulin.

31. The device of claim 1, wherein a first polypeptide is GLP-1 and a second polypeptide is PYY.

* * * * *